US012697416B2

(12) United States Patent
Boughton et al.

(10) Patent No.: US 12,697,416 B2
(45) Date of Patent: Aug. 4, 2026

(54) REINFORCED BIOCOMPATIBLE SCAFFOLD

(71) Applicant: GLOBAL SURGICAL INNOVATIONS PTY LTD, Burwood (AU)

(72) Inventors: Elizabeth Anne Boughton, Burwood (AU); Philip Boughton, Burwood (AU)

(73) Assignee: Global Surgical Innovations Pty Ltd, Burwood (AU)

( * ) Notice: Subject to any disclaimer, the term of this patent is extended or adjusted under 35 U.S.C. 154(b) by 1216 days.

(21) Appl. No.: 17/432,537

(22) PCT Filed: Feb. 21, 2020

(86) PCT No.: PCT/AU2020/050158
§ 371 (c)(1),
(2) Date: Aug. 20, 2021

(87) PCT Pub. No.: WO2020/168394
PCT Pub. Date: Aug. 27, 2020

(65) Prior Publication Data
US 2022/0143271 A1     May 12, 2022

(30) Foreign Application Priority Data

Feb. 22, 2019   (AU) ................................ 2019900565

(51) Int. Cl.
| | |
|---|---|
| *A61L 27/56* | (2006.01) |
| *A61L 27/38* | (2006.01) |
| *A61L 27/44* | (2006.01) |
| *A61L 27/48* | (2006.01) |
| *A61L 27/54* | (2006.01) |
| *A61L 27/58* | (2006.01) |
| *A61L 27/60* | (2006.01) |

(Continued)

(52) U.S. Cl.
CPC ......... *A61L 27/3834* (2013.01); *A61L 27/446* (2013.01); *A61L 27/48* (2013.01); *A61L 27/54* (2013.01); *A61L 27/56* (2013.01); *A61L 27/58* (2013.01); *A61L 27/60* (2013.01); *A61L 2300/232* (2013.01); *A61L 2300/236* (2013.01); *A61L 2300/252* (2013.01); *A61L 2300/406* (2013.01); *A61L 2300/414* (2013.01); *A61L 2300/64* (2013.01); *A61L 2400/12* (2013.01); *C12N 5/0068* (2013.01); *C12N 5/0602* (2013.01); *C12N 2533/12* (2013.01); *C12N 2533/40* (2013.01)

(58) Field of Classification Search
CPC ...................................................... A61L 27/56
See application file for complete search history.

(56) References Cited

U.S. PATENT DOCUMENTS

2017/0312080 A1* 11/2017 Sheth ...................... A61L 31/10

FOREIGN PATENT DOCUMENTS

WO       WO-2008134807 A1 * 11/2008 ............ C08J 9/0004

* cited by examiner

*Primary Examiner* — Cachet I Proctor
(74) *Attorney, Agent, or Firm* — Morgan, Lewis & Bockius LLP

(57) ABSTRACT

A reinforced biocompatible scaffold facilitates integration of biological tissue. The reinforced scaffold comprises a porous biocompatible scaffold and an arrangement of at least one biocompatible filament embedded within and fixed to the biocompatible scaffold, and/or at least one biocompatible conduit embedded within and fixed to the biocompatible scaffold.

15 Claims, 4 Drawing Sheets

(51) Int. Cl.

| | | |
|---|---|---|
| *C12N 5/00* | | (2006.01) |
| *C12N 5/071* | | (2010.01) |

100

<u>200</u>

REINFORCED BIOCOMPATIBLE SCAFFOLD

FIELD OF THE INVENTION

The present invention relates to tissue scaffolds and in particular to a porous bioabsorbable composite scaffold, a bioabsorbable pump, a tissue repair system, a method of manufacturing a porous bioabsorbable composite scaffold, a method of increasing the density of a porous bioabsorbable composite scaffold, a method of joining two porous bioabsorbable composite scaffolds and a method of manufacturing a porous bioabsorbable composite scaffold having graded porosity.

The invention has been developed primarily for use in laboratory and clinical applications such as cell culture, tissue engineering, fracture and wound healing, defect filling and vascular applications and will be described hereinafter with reference to these applications. However, it will be appreciated that the invention is not limited to these particular fields of use.

BACKGROUND OF THE INVENTION

Tissue engineering is an emerging and rapidly developing field, involving the repair, replacement and substitution of damaged or diseased tissues. Wound healing and defect filling involve the implantation of a scaffold into the wound or defect to promote the regeneration of natural tissue into the wound or defect location. Many scaffold features necessary and desirable for use in tissue engineering, wound healing or defect filling are known.

Important requirements include biocompatibility, biodegradability, processability, sterilisability and suitable mechanical strength for the particular application (Hou Q, Grijpma O W, Feijen J. Preparation of interconnected highly porous polymeric structures by a replication and freeze-drying process. *J Biomed Mater Res B Appl Biomater.* 2003; 67(2): 732-40). In addition to these requirements, it has generally been found that a high porosity and a high interconnectivity is also desirable, as this increases the surface area of the scaffold and makes it more conducive to cell attachment and tissue ingrowth.

Moreover, an appropriate pore size range and distribution is also thought to be beneficial, as macropores help govern scaffold mechanical properties, tissue architecture, vascularisation and promote the infiltration of cells into the scaffold, whilst mesopores and nanopores affect the surface energy of the cell interfaces of the scaffold (which, in turn affects the wetting, adsorption, degradation, ion release and buffering properties), impacting on the function, attachment, proliferation and migration of cells into the scaffold.

Known tissue engineering, wound healing and defect filling scaffolds are classifiable into three broad categories:
(1) hydrogels,
(2) foams, and
(3) three-dimensional (3D) meshes and fabrics.

An example of a hydrogel-containing product is the PELNAC Artificial Dermis composed of an inner sponge layer of collagen hydrogel and an outer layer of silicone. The elastin can be made into gels, fibre, closed foam, film, sheets, tubes and bands to be used as surgical devices, device coatings, consumables in tissue culture or as an injectable material. Another example is the ProPatch® Soft Tissue Repair Matrix, a decellularised bovine pericardium based surgical mesh made by Cryoltfe, Inc.

Foams are a broad category that encompasses numerous products made from a range of polymers, ceramics, metals and composites using a range of fabrication methods. Foams made from bioactive ceramics, such as calcium phosphate and bioactive glass, while able to stimulate hard and soft tissue growth, tend to be brittle and cause stress shielding.

Polymers are often favoured due to their toughness and versatility in processing stemming from their relatively low glass transition temperatures and melting temperatures. For example, polymers are able to be relatively easily processed into 3D meshes and fabrics using fibre bonding, solid free-form fabrication or rapid prototyping techniques, and into porous foam structures using moulding, gel casting, solution casting, replication or solvent casting and particulate leaching techniques (using various porogens such as sugar, sodium chloride, ammonium chloride and paraffin) (see for example Agrawal C M, Ray RB. Biodegradable polymeric scaffolds for musculoskeletal tissue engineering. J Biomed Mater Res. 2001; 55(2): 141-50; Grenier S, Sandig M, Mequanint K. Polyurethane biomaterials for fabricating 3D porous scaffolds and supporting vascular cells. J Biomed Mater Res A. 2007; 82(4): 802-9; Hou Q, Grijpma O W, Feijen J. Preparation of interconnected highly porous polymeric structures by a replication and freeze-drying process. J Biomed Mater Res B Appl Biomater. 2003; 67(2): 732-40). In general, however, unlike many silicate ceramics, synthetic polymers are not bioactive and thus do not biochemically promote the attachment and proliferation of cells and tissues.

Composite materials allow the physical, mechanical and biochemical properties of scaffolds to be customised. For example, polymer and bioactive glass-based composites are being increasingly investigated. In one example, Day et al (Day R M, Boccaccini A R, Shurey S, Roether J A, Forbes A, Hench L L, Gabe S M. Assessment of polyglycolic acid mesh and bioactive glass for soft-tissue engineering scaffolds. Biomateria/s. 2004; 25(27): 5857-66) investigated the in vitro and in vivo effect on the growth of soft tissues of integrating a bioactive glass phase into sheets of knitted polyglycolic acid (PGA) mesh. In another example, Li et al (Li X, Shi J, Dong X, Zhang L, Zeng H. A mesoporous bioactive glass/polycaprolactone composite scaffold and its bioactivity behavior. J Biomed Mater Res A. 2008; 84(1): 84-91) used a solvent casting-particulate leaching technique with sodium chloride as the porogen to fabricate polycaprolactone and sol-gel derived bioactive glass composite scaffolds.

Currently known skin replacement or skin graft products include human or bovine biologically derived or biological and synthetic composite skin replacement products (see products made by Organogenesis Inc. and Integra), synthetic elastin skin replacement products (see products made by Elastagen Ply Ltd) and biodegradable polyurethanes (see products made by Po/yNovo Biomaterials Ply Ltd). Bone filler, 30 cell culture and tissue engineering products made from polycaprolactone are commercially known, such as meshes made by Osteopore and 3D Bialek.

The present invention seeks to provide a porous bioabsorbable composite scaffold, a bioabsorbable pump, a tissue repair system, a method of manufacturing a porous bioabsorbable composite scaffold, a method of increasing the density of a porous bioabsorbable composite scaffold, a method of joining two porous bioabsorbable composite scaffolds and a method of manufacturing a porous bioabsorbable composite scaffold having graded porosity, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE INVENTION

According to a first aspect of the present invention, a porous bioabsorbable composite scaffold is provided, comprising a polymeric component and one or more bioactive components and having a generally random arrangement of struts defining an interconnected network of pores.

Advantageously, the scaffold is suitable for use in laboratory and clinical applications such as cell culture, tissue engineering, fracture and wound healing and defect filling.

Advantageously, polymers are relatively tough, compressible and elongatable and easily processable due to their relatively low glass transition temperatures and melting temperatures.

Advantageously, the addition of one or more bioactive components to a scaffold having a polymeric component enhances the bioactivity of the scaffold and allows the degradation rate and the mechanical properties of the scaffold to be controlled, for example by varying the relative amounts of the polymeric and bioactive components or by altering the physical structure of the scaffold.

Furthermore, a mesh or periodically repeating array of strut connections is more susceptible to buckling instability when compressed, sheared or torsioned along a range of different orthogonal and non-orthogonal axes. This is caused by a progressive increase in strain until buckling occurs, at which point the scaffold substantially loses its ability to provide structural support. An advantage of providing a scaffold having a generally random arrangement of struts is that it is better able to support substantial compressive, shear and rotational strain along different orthogonal and non-orthogonal axes with proportional increments in stress.

The elastic modulus of the scaffold can be customised to generally match or be slightly stiffer than the modulus of soft tissue.

The interconnected network of pores may be macroporous.

Advantageously, macropores help govern scaffold mechanical properties and tissue architecture and vascularisation, and promote the infiltration of cells, vessels and connective tissue into the scaffold.

The network of pores may be nanoporous.

The network of pores may be mesoporous.

Advantageously, mesopores and nanopores affect the surface energy of the cell interfaces of the scaffold (which, in turn affects the wetting, adsorption, degradation, ion release and buffering properties) impacting on the function, attachment proliferation and migration of cells into the scaffold.

At least one of the one or more bioactive components may be coated on the polymeric component.

The one or more bioactive components may be located directly at the cell interface.

At least one of the one or more bioactive components may be incorporated within the polymeric component.

The at least one of the one or more bioactive components can take the form of a nano, meso or micro particle or fibre.

Advantageously, the degradation rate and mechanical properties are easily controlled and are stable over a relatively extended period of time during degradation.

The relative amount of the at least one of the one or more bioactive components may be graded within the polymeric component.

Advantageously, this allows the bioactivity, degradation rate and mechanical properties of 10 the scaffold to be graded, which is desirable if, for example, the scaffold is used to interface different types of tissue to either side.

At least one of the one or more bioactive components may be a bioactive glass.

Advantageously, bioactive glass is also able to be coated on and incorporated into polymer structures. Coating or incorporating bioactive glass into the scaffold provides or improves the soft and hard tissue bonding capabilities of the scaffold.

Another advantage of having a bioactive glass component is the ability of bioactive glass to buffer the acidic environment caused by polymer degradation products.

Furthermore, in general, bioactive glass has a relatively high degradation rate. Thus, coating or incorporating varying amounts of a bioactive glass phase into the scaffold allows the degradation rate of the scaffold to be customised.

The bioactive glass may be powdered.

Advantageously, adding bioactive glass in relatively small particles provides a large reactive surface area for enhanced bioactivity.

The bioactive glass may be coated with a therapeutic substance.

In one embodiment, the bioactive glass may be coated with a bone morphogenic protein (BMP). Bone morphogenic proteins assist with hard and soft tissue repair and can be advantageously introduced into the scaffold as a coating on the bioactive glass as they readily adhere to hydrated surface layers that form on bioactive glasses in use.

The porous bioabsorbable composite scaffold may have a graded porosity.

Advantageously, modifying the porosity of the scaffold may affect its degradation rate and mechanical properties. For in vivo applications, providing a scaffold of graded porosity supports tissue transitions, that is, if the scaffold is used to interface different types of tissue to either side of it. In one example, the scaffold may be used to interface derma to one side and subcutaneous tissue or fat to the other side. In another example, the scaffold may be used to interface cartilage to one side and bone to the other side. In another example, the scaffold may be used to interface tendon to one side and bone to the other side. For in vitro applications, a scaffold of graded porosity may be useful in cell culture to determine optimum porosities for particular cell types. The porosity of the scaffold can be graded to various extents. In one example, the gradient of the porosity may be linear.

The polymeric component may be polycaprolactone.

Advantageously, polycaprolactone (PCL) is a bioabsorbable and soft and hard tissue compatible material. As with many polymers, its low melting point and glass transition temperature facilitates relatively easy processability. Even compared to polymers used in similar applications, such as polyglycolide (PLGA), poly(DL-lactide) (DL-PLA), poly (L-lactide) (L-PLA) and polyglycolic acid (PGA), the relatively lower melting point of polycaprolactone of 58-63° C. allows it to be processed at temperatures that are easily achievable in a common laboratory or clinical setting. Additionally, having a relatively low elastic modulus of 0.21-0.34 MPa that is comparable to that of human skin, which has an elastic modulus of 0.2-3 MPa, makes it very suitable for use as a component in a soft tissue scaffold. This reduces or eliminates the amount of trauma caused to neighbouring soft tissues and reduces or eliminates stress shielding in bone.

Furthermore, PCL is able to achieve large elongations before fracturing while withstanding substantial shear and tensile forces. Skin grafts are often subjected to such forces and thus PCL is suitable for skin replacement and grafting applications. Polycaprolactone also has a relatively low rate of degradation, allowing more stable resorption and wound healing as it elicits milder inflammatory responses and foreign body reactions in comparison to materials with high rates of degradation.

Preferably, the polymeric component is polycaprolactone combined with one or more polymer modifiers.

Advantageously, PCL may be modified to produce a more desirable degradation profile.

At least one of the one or more polymer modifiers may be polylactic acid or polyvinyl pyrrolidone.

Advantageously, modified polymers are generally stronger and have higher elastic moduli. Thus, the polymeric component of the scaffold will be stronger and have a higher elastic modulus if made of polycaprolactone combined with one or more polymer modifiers.

At least one of the one or more bioactive components may be sugar.

At least one of the one or more bioactive components may be caramelised sucrose.

Advantageously, sugar and caramelised sucrose can be broken down and used by cells as an energy source. When placed in contact with cells, sugar and caramelised sucrose help regulate the biological functions and the quality and quantity of cell-to-cell interaction. Additionally, carameralised sucrose has antibacterial properties.

At least one of the one or more bioactive components may be an antibiotic.

Advantageously, antibiotics kill or inhibit the growth of bacteria. If the scaffold is used in a wound healing or defect filling application, this prevents the wound or defect from becoming infected, which prevents or slows healing.

At least one of the one or more bioactive components may be a growth factor or a combination of a plurality of growth factors.

Advantageously, growth factors stimulate cellular growth, proliferation and cellular differentiation by regulating a variety of cellular processes.

At least one of the one or more bioactive components may be a bioactive honey or a wax derived from a honey.

Advantageously, bioactive honey (medihoney) may be used to assist with the dermal wound healing properties of the scaffold. In general, honey has antibacterial properties stemming from its relatively low pH of 3.2 to 4.5, and thus it prevents and inhibits the growth of micro-organisms. Honey also assists tissue repair due to its hyperosmolarity and stimulating of body enzymes, which promotes the removal of necrotic tissue in the wound. Furthermore, honey releases hydrogen peroxide, which promotes the formation of new blood vessels and fibroblast, thus increasing the rate at which granulation tissue is created.

The porous bioabsorbable composite scaffold may further comprise one or more additive components.

Advantageously, providing one or more additive components improves the properties, functionality and/or versatility of the scaffold.

At least one of the one or more additive components may be a radio-opaque component.

Advantageously, the form and position of the scaffold may be monitored using x-ray during and following implantation.

The radio-opaque component comprises barium sulphate particles or barium-modified bioactive glass particles.

Advantageously, barium sulphate is a widely accepted, clinically used radiocontrast agent that has little to no harmful impact on the body. Low amounts of barium in bioactive glass increases the radio-opacity of bioactive glass and also has little to no harmful impact on the body.

Preferably, at least one of the one or more additive components may be a magnetic component.

Advantageously, the addition of a magnetic component allows the scaffold to be actuated and vibrated using an externally applied magnetic field. This is useful for in vitro mechanical actuation. Moreover, mechanical movement of the scaffold in vivo stimulates the surrounding tissue enhances wound healing. Moving the scaffold may also provide a pumping action which assists the removal of neutrophils (pus) from the wound site, thereby accelerating the rate of healing.

The magnetic component may comprise at least one selected from the following group of:
    (i) pure iron particles
    (ii) ferrous oxide particles, and
    (iii) ferric oxide particles.

Advantageously, pure iron particles, ferrous (II) oxide particles and ferric (III) oxide particles are magnetic and are biocompatible.

At least one of the one or more additive components may be an electrically conductive component.

Advantageously, addition of an electrically conductive component allows electrical charge to be evenly dispersed within the scaffold when used as an electrode base for muscle actuation. This is useful in vascular and functional electrical stimulation (FES) applications.

The electrically conductive component may comprise at least one selected from the following group:
    (i) magnesium based glass particles,
    (ii) iron based glass particles, and
    (iii) calcium based glass particles.

Advantageously, magnesium glass particles, iron glass particles and calcium glass particles are electrically conductive and are biocompatible.

At least one of the one or more additive components may be a piezoelectric component.

Advantageously, addition of a piezoelectric component causes the scaffold to produce a slight potential difference when mechanically strained. This allows the scaffold to act as a sensor for strain and mechanical manipulation in vivo, facilitating its use as a diagnostic device for monitoring fracture or wound healing processes.

The piezoelectric component may be a piezoelectric crystal.

The piezoelectric component may be a piezoelectric polymer.

The piezoelectric component may be a piezoelectric ceramic.

The piezoelectric ceramic may be a lead-free piezoelectric ceramic.

The piezoelectric ceramic may comprise at least one selected from the following group:
    (i) magnesium based glass,
    (ii) iron based glass, and
    (iii) calcium based glass.

Advantageously, magnesium glass, iron glass and calcium glass are piezoelectric and electrically conductive and are biocompatible.

Preferably, at least one of the one or more additive components is a biocompatible polymer-coated magnetic component.

Preferably, the biocompatible polymer-coated magnetic component comprises at least one material from the following group of materials:

(i) biocompatible polymer-coated ferrous(II) oxide particles, and (ii) biocompatible polymer-coated ferrous(II) oxide particles.

At least one of the one or more additive components may be a biocompatible glass-coated magnetic component.

The biocompatible glass-coated magnetic component may comprise at least one selected from the following group of materials:

(i) biocompatible glass-coated ferrous$_{(III)}$ oxide particles, and (ii) biocompatible glass-coated ferric$_{(III)}$ oxide particles.

At least one of the one or more additive components may be a biocompatible silicon-coated magnetic component.

The biocompatible silicon-coated magnetic component may comprise at least one selected from the following group:

(i) biocompatible silicon-coated ferrous$_{(III)}$ oxide particles, and (ii) biocompatible silicon-coated ferric$_{(III)}$ oxide particles.

Advantageously, the addition of a biocompatible polymer-coated, glass-coated or silicon-coated magnetic component imparts similar advantages to the addition of a magnetic component, as described above. Furthermore, mechanically actuating the biocompatible polymer-coated, glass-coated or silicon-coated magnetic component facilitates the degradation of the scaffold at an accelerated rate. For example, this can be achieved by subjecting the scaffold to an oscillating remote magnetic field. Moreover, coating magnetic particles with polymer, glass or silicon prevents or retards the degradation of the magnetic particles, thus extending the longevity of the magnetic functionality of the scaffold. It also isolates the magnetic particles from tissues when the scaffold is in use. For example, despite the biocompatibility and relatively slow degradation rate of pure iron particles, ferrous oxide particles and ferric oxide particles, it is still desirable in some instances to prevent direct contact between the particles and tissues, especially in in vitro culture and tissue engineering applications. The depending on the specific composition used, the coating can be stable to prevent degradation or dissolvable to still allow the disappearance of foreign particles within the body over time.

At least one of the one or more additive components may be a biocompatible polymer-coated electrically conductive component.

The biocompatible polymer-coated electrically conductive component may comprise at least one selected from the following group:

(i) biocompatible polymer-coated iron particles, (ii) biocompatible polymer-coated calcium particles, and (iii) biocompatible polymer-coated magnesium particles.

The at least one of the one or more additive components may be a biocompatible glass-coated electrically conductive component.

The biocompatible glass-coated electrically conductive component may comprise at least one selected from the following group:

(i) biocompatible glass-coated iron particles, (ii) biocompatible glass-coated calcium particles, and (iii) biocompatible glass-coated magnesium particles.

The at least one or more additive components may be a biocompatible silicon-coated electrically conductive component.

The biocompatible silicon-coated electrically conductive component may comprise at least one material from the following group of materials:

(i) biocompatible silicon-coated iron particles, (ii) biocompatible silicon-coated calcium particles, and (iii) biocompatible silicon-coated magnesium particles.

Advantageously, the addition of a biocompatible polymer-coated, glass-coated or silicon-coated electrically conductive component imparts similar advantages to the addition of an electrically conductive component, as described above. In addition to this, mechanically actuating and/or inducing a potential difference in the biocompatible polymer-coated, glass-coated or silicon-coated electrically conductive component facilitates the degradation of the scaffold at an accelerated rate. For example, this can be achieved by subjecting the scaffold to an oscillating remote magnetic field. Moreover, coating electrically conductive particles with polymer, glass or silicon prevents or retards the degradation of the electrically conductive particles, thus extending the longevity of the electrically conductive functionality of the scaffold. It also isolates the electrically conductive particles from tissues when the scaffold is in use. For example, despite the biocompatibility of iron, calcium and magnesium particles, it is still desirable in some instances to prevent direct contact between the particles and tissues, especially in in vitro culture and tissue engineering applications. The depending on the specific composition used, the coating can be stable to prevent degradation or dissolvable to still allow the disappearance of foreign particles within the body over time.

Advantageously, iron particles, calcium particles and magnesium particles are electrically conductive and are biocompatible.

The porous bioabsorbable composite scaffold may further comprises a soluble, structurally supportive, temporary filler component adapted to prevent deformation of the scaffold during transport, delivery and/or implantation.

Advantageously, this prevents damage to the scaffold by allowing it to maintain its structure and shape during transport, delivery and implantation.

The soluble structurally supportive temporary filler component may be a sugar.

Advantageously, sugar is stiff and will substantially provide structural support to the scaffold. Furthermore, sugar is capable of dissolving in vivo and can deliver bioactive molecules or proteins.

The porous bioabsorbable composite scaffold may be adapted to be sterilised by ultraviolet or gamma irradiation.

Advantageously, this is required in order to allow the scaffold to prevent the introduction of foreign micro-organisms in vitro or in vivo. Furthermore, exposing polymers to ultraviolet or gamma radiation affects the degradation rate of the polymer in biological fluids, depending on the radiation dosage and type. Exposure to radiation has also been shown to affect the elastic modulus of the exposed polymer. These effects allow the use of radiation to have a dual purpose. The first is sterilisation of the scaffold, and the second is the manipulation or customisation of the physical properties of the polymeric component of the scaffold. In addition to this, exposing polycaprolactone with gamma rays causes it to cross-link. The extent of cross-linking, and thus the associated mechanical properties of the scaffold, can be controlled by manipulating the dosage of the gamma radiation.

The porous bioabsorbable composite scaffold may further comprise a dehydrated hydrogel or hydrocolloid component adapted to increase in volume when hydrated.

Advantageously, the dehydrated hydrogel or hydrocolloid component will prevent deformation of the scaffold during transport, delivery and/or implantation, which prevents it from being damaged.

The porous bioabsorbable composite scaffold may be adapted to be compressed and expands when the dehydrated hydrogel or hydrocolloid is hydrated.

Advantageously, as well as preventing the deformation of the scaffold during transport, delivery and/or implantation, a pre-compressed or pre-shrunk scaffold will be more easily implanted and positioned in vivo. The scaffold will expand on exposure to the biological fluids to fill defects or fractures or close wounds as it is hydrated, leading to a reduced chance of collapse and expulsion from the defect, fracture or wound.

The porous bioabsorbable composite scaffold may be adapted to absorb an in vivo additive component delivered in vivo subsequent to the implantation of the porous bioabsorbable scaffold.

Advantageously, additive components, such as donor cells or tissues, therapeutic substances or bioactive substances, may be delivered to directly to the implant site to accelerate healing. This is particularly useful if continual delivery of additive components is desired or required, for example, regular courses of antibiotics, or if bioactive components quickly degrade and need to be replenished.

The in vivo additive component may comprise at least one substance from the following group of substances:

(i) a hydrogel,
(ii) a protein,
(iii) cells,
(iv) a tissue, and
(v) stem cells.

Advantageously, delivering bioactive components such as hydrogels and proteins help promote the differentiation, attachment and/or proliferation of cells at the fracture, defect or wound site. Delivering additive components in vivo such as cells, tissues and stem cells helps replenish the cell stock at the site. Furthermore, being able to deliver additive component post-implantation allows the substances to be replenished as desired.

According to a second aspect of the present invention, a bioabsorbable pump is provided, comprising a porous bioabsorbable composite scaffold, an outer membrane covering the scaffold, an inlet located through the outer membrane having a first unidirectional valve, and an outlet located through the outer membrane having a second unidirectional valve, the first unidirectional valve being adapted to allow fluid to enter the scaffold and the second unidirectional valve being adapted to allow fluid to exit the scaffold when the pressure within the scaffold exceeds a threshold value.

Advantageously, the pump facilitates the perfusion of biological fluids and nutrients through and the removal of waste from an area, such as in the intervertebral disc. This is particularly beneficial for areas with reduced capacity for biological fluids, nutrient and waste cycling, due to damage or disease. On the other hand, enhancing such bodily functions allows wound, fracture or defect healing to be accelerated. In an in vitro application, the pump can be used as a bioreactor, supporting a biologically active environment and simulating in vivo conditions.

The first and second unidirectional valves may be leaflet valves.

Advantageously, leaflet valves have a simple mechanical design and cause relatively little or no damage to cells, making it particularly suitable for use in the body.

The pressure within the scaffold may be increased to the threshold value by subjecting the bioabsorbable pump to a compressive force.

Advantageously, the pump is able to be activated by a simple mechanical action. This mechanical action may be deliverable by the natural body movement of the individual in whom the scaffold is implanted. This compressive force may also be supplied by a simple mechanical actuator for ex vivo applications.

The pressure within the scaffold may be increased to the threshold value by applying a magnetic field or an electromagnetic field.

Advantageously, the pump is able to be actuated magnetically or electromagnetically. Thus, the pump may be activated by external, remote means, which may be desirable if it has been implanted in the body.

The outer membrane may be substantially made of a polymer.

Advantageously, polymers are relatively tough, compressible and elongatable and easily processable due to their relatively low glass transition temperatures and melting temperatures.

The outer membrane may be substantially made of a polymeric composite.

Advantageously, the use of a polymeric composite allows the physical, mechanical and biochemical properties of the scaffold to be more customisable and controllable.

According to a third aspect of the present invention, a tissue repair system is provided, comprising:

a first membrane layer, a second membrane layer, and an intermediate layer joined to and located intermediate the first and second membrane layers and made substantially of a porous bioabsorbable composite scaffold.

Advantageously, the first and second membrane layers of the tissue repair system can be customised in terms of permeability, elastic modulus and strength for specific applications. For example, differentiating the properties of the first and second membrane layers allow the tissue repair system to better support tissue transitions, e.g. derma to fat transitions or connective tissue to bone transitions.

The first membrane layer may be an elastic semi-permeable membrane.

Advantageously, a membrane that is elastic and semi-permeable is suitable for use as an outer layer for a synthetic skin graft, allowing gas exchange and a small amount of moisture loss, but preventing infection and wound breach.

The second membrane layer may be a permeable membrane.

Advantageously, a membrane that is permeable is suitable for interfacing with internal tissues, such as organs, connective/vascular tissues or bone.

The second membrane layer may be a semi-permeable membrane.

Advantageously, the tissue repair system can be used for closing or repairing a surface wound.

The first membrane layer may be made from a polymer.

Advantageously, polymers are relatively tough, compressible and elongatable and easily processable due to their relatively low glass transition temperatures and melting temperatures.

The polymer may be polycaprolactone.

Advantageously, polycaprolactone (PCL) is a bioabsorbable and soft and hard tissue compatible material, with a low melting point and glass transition temperature, a relatively low elastic modulus, a high ductility and a relatively low rate of degradation.

The first membrane layer may be made from a polymeric composite.

Advantageously, the use of a polymeric composite allows the physical, mechanical and biochemical properties of the membrane layer to be more customisable and controllable.

The polymeric composite may be a polycaprolactone-bioactive-glass composite.

Advantageously, coating or incorporating bioactive glass into the membrane layer provides or improves the soft and hard tissue bonding capabilities of the membrane layer. Furthermore, the degradation of the bioactive glass serves to buffer the acidic environment caused by polymer degradation products.

The bioactive glass may take the form of bioactive glass nano-particulates.

Advantageously, adding bioactive glass in relatively small particles provides a large reactive surface area for enhanced bioactivity.

The second membrane layer may be made from a polymer.

Advantageously, polymers are relatively tough, compressible and elongatable and easily processable due to their relatively low glass transition temperatures and melting temperatures.

The polymer may be polycaprolactone.

Advantageously, polycaprolactone (PCL) is a bioabsorbable and soft and hard tissue compatible material, with a low melting point and glass transition temperature, a relatively low elastic modulus, a high ductility and a relatively low rate of degradation.

The second membrane layer may be made from a polymeric composite.

Advantageously, the use of a polymeric composite allows the physical, mechanical and biochemical properties of the membrane layer to be more customisable and controllable.

The polymeric composite may be a polycaprolactone-bioactive-glass composite.

Advantageously, coating or incorporating bioactive glass into the membrane layer provides or improves the soft and hard tissue bonding capabilities of the membrane layer. Furthermore, the degradation of the bioactive glass serves to buffer the acidic environment caused by polymer degradation products.

The bioactive glass may take the form of bioactive glass fibres.

Advantageously, reinforcing a polymer membrane with bioactive glass fibres improves the tensile modulus and strength of the membrane.

The bioactive glass may take the form of bioactive glass nano-particulates.

Advantageously, adding bioactive glass in relatively small particles provides a large reactive surface area for enhanced bioactivity.

According to a fourth aspect of the present invention, a tissue repair system is provided, comprising:

a core made substantially of a porous bioabsorbable composite scaffold, and a sheath enclosing the core and being substantially made of an elastic semi-permeable membrane.

Advantageously, the tissue repair system can be used for closing or repairing a surface wound, allowing gas exchange and a small amount of moisture loss, but preventing infection and wound breach.

According to a fifth aspect of the present invention, a method of manufacturing a porous bioabsorbable composite scaffold is provided, comprising the following steps:

dissolving at least polycaprolactone in an organic solvent to form an at least polycaprolactone solution.

immersing a porogen construct in the at least polycaprolactone solution to form a temporary composite comprising at least organic solvent, porogen material and a polycaprolactone structure; and removing the temporary composite from the at least polycaprolactone solution.

Advantageously, dissolving at least polycaprolactone (PCL) in an organic solvent to form an at least polycaprolactone solution and immersing the porogen construct in the at least polycaprolactone solution facilitates the infiltration of polycaprolactone into the interstices of the porogen construct. The porogen construct provides a template or a negative mould for the scaffold.

The organic solvent may be acetone.

Advantageously, acetone is found naturally in the body as a product of the metabolism of fats and is therefore not toxic to the body in trace amounts, unlike many organic solvents. Moreover, acetone is available at a relatively low cost compared to many other organic solvents.

The porogen construct may comprise a sugar construct.

Advantageously, the sugar construct provides an interconnected network of pores with a high degree of porosity and a substantially random arrangement of struts for support, making it suitable as a template for the scaffold. Furthermore, sugar is a biocompatible and bioactive material and thus allowing the sugar to remain either in bulk or in trace amounts is not detrimental to and may enhance cellular growth and proliferation. Sugar also advantageously provides nutrition for cells and limits bacterial growth, and thus will accelerate the wound healing capabilities of the scaffold.

The sugar construct may comprise at least one sugar selected from the following group of sugars:

(i) sucrose, (ii) glucose, (iii) fructose, (iv) galactose, and (v) casein.

Advantageously, the sugars listed above are naturally occurring sugars found in the body.

The porogen construct may comprise a salt construct.

Advantageously, the salt construct is able to be provided having an interconnected network of pores with a high degree of porosity and substantially random arrangement of struts for support, making it suitable as a template for the scaffold. Furthermore, use of biocompatible salts are not detrimental to and may enhance cellular growth and proliferation.

The salt construct may comprise at least one salt from the following group of salts:

(i) sodium chloride, (ii) calcium phosphate, and (iii) monosodium glutamate.

Advantageously, the salts listed above are naturally occurring salts and provide nutrition for wound healing. In particular, calcium phosphate forms an anisotropic solid having needle-like formations and monosodium glutamate (MSG) forms an anisotropic solid having rod-like formations. Thus, scaffolds formed from a calcium phosphate or monosodium glutamate constructs will also be anisotropic, which can be advantageous for providing directionality. Depending on the porogen used, scaffolds of differing connective strut arrays can be manufactured. Monosodium glutamate has also been shown to have neural stimulative properties.

The method of manufacturing a porous bioabsorbable composite scaffold may further comprise the step of:

removing an outer membrane from the temporary composite to leave an at least polycaprolactone structure.

The membrane is a layer of residual polycaprolactone that is removed to advantageously facilitate further scaffold processing.

The method of manufacturing a porous bioabsorbable composite scaffold may further comprise the following step:

drying the scaffold.

Step (v) or drying the scaffold may include centrifuging the at least polycaprolactone structure and blowing the at least polycaprolactone structure with clean, filtered air.

Advantageously, drying the scaffold in clean, filtered air prevents or reduces the introduction of contaminants into the polycaprolactone structure and is an effective and cost-effective method of drying the scaffold. In one example, the air can be cleaned and filtered using a HEPA filter. The at least polycaprolactone structure can then be transported, delivered and implanted without removal of the porogen material. The stiffness of the porogen material prevents deformation of the structure and can be removed prior to implantation or implanted as it is.

The method of manufacturing a porous bioabsorbable composite scaffold may further comprise the following additional step prior to step (v):

dissolving and washing out the porogen material and organic solvent from within the temporary composite to substantially remove the porogen material and organic solvent from the at least polycaprolactone structure.

Advantageously, the porogen material and organic solvent can be removed, allowing the at 10 least polycaprolactone structure to be used as a porous bioabsorbable scaffold.

The additional step may include washing the at least polycaprolactone structure in water.

Advantageously, removing the porogen material and organic solvent comprises a simple step of washing it in water, for example under running water, which can be easily performed in the laboratory.

The at least polycaprolactone structure may be washed in water for at least 30 minutes.

The at least polycaprolactone structure may be washed in water for at least 1 hour.

The at least polycaprolactone structure may be washed in water for at least 12 hours.

Advantageously, washing the at least polycaprolactone structure under water for an extended period of time ensures the removal of all or at least a substantial portion of the porogen material and organic solvent.

The additional step may include soaking the at least polycaprolactone structure in a water bath and rinsing repeatedly.

Advantageously, soaking the at least polycaprolactone structure ensures that all or at least a substantial amount of the porogen material is dissolved and rinsing the at least polycaprolactone structure flushes away porogen material and organic solvent. Advantageously, this step can be easily performed in the laboratory.

The method of manufacturing a porous bioabsorbable composite scaffold may further comprise the following steps after step (i):

heating the at least polycaprolactone solution, and stirring the at least polycaprolactone solution to ensure an even consistency.

Advantageously, ensuring that the at least polycaprolactone solution has an even consistency will improve the quality, reliability and consistency of the end product, as the density of polycaprolactone will be more constant throughout the scaffold.

Step (ii) may include immersing the porogen construct in the at least polycaprolactone solution for a period of at least 5 minutes.

The porogen construct may be immersed in the at least polycaprolactone solution for a period of at least 10 minutes.

The porogen construct may be immersed in the at least polycaprolactone solution for a period of at least 1 hour.

The porogen construct may be immersed in the at least polycaprolactone solution for a period of at least 6 hours.

The porogen construct may be immersed in the at least polycaprolactone solution for a period of at least 12 hours.

The porogen construct may be immersed in the at least polycaprolactone solution for a period of at least 24 hours.

Advantageously, immersing the porogen construct for an extended period of time allows the at least polycaprolactone solution to completely infiltrate the interstices of the porogen construct, thereby allowing the formation of a more structurally regular scaffold. Immersing the porogen construct in the at least polycaprolactone solution for an extended period of time also results in the formation of a scaffold having smaller struts.

Step (ii) may includes heating the at least polycaprolactone solution and the immersed porogen construct.

Advantageously, heating the at least polycaprolactone solution and the immersed porogen construct better facilitates the infiltration of the at least polycaprolactone solution into the interstices of the porogen construct.

Step (ii) may include microwaving the at least polycaprolactone solution and the immersed porogen construct.

Advantageously, microwaving the at least polycaprolactone solution and the immersed porogen construct better facilitates the infiltration of the at least polycaprolactone solution into the interstices of the porogen construct.

Step (ii) may includes centrifuging the at least polycaprolactone solution and the immersed porogen construct.

Advantageously, centrifuging the at least polycaprolactone solution and the immersed porogen construct better facilitates the infiltration of the at least polycaprolactone solution into the interstices of the porogen construct.

Step (ii) may include agitating the at least polycaprolactone solution and the immersed porogen construct.

Advantageously, agitating the at least polycaprolactone solution and the immersed porogen construct better facilitates the infiltration of the at least polycaprolactone solution into the interstices of the porogen construct.

The method of manufacturing a porous bioabsorbable composite scaffold may further comprise the following steps after step (v):

coating the at least polycaprolactone structure with bioactive glass powder.

Advantageously, introducing bioactive glass into the scaffold will stimulate both soft and hard tissue bonding to the scaffold when implanted. The bioactive glass will also help buffer the acidic environment caused by polycaprolactone degradation products. Varying the relative amounts of polycaprolactone and bioactive glass allows the degradation rate of the scaffold to be customised.

Coating bioactive glass powder to the scaffold is a simple and effective method of introducing bioactive glass into the scaffold, and furthermore, has the advantage of locating the bioactive substance at the tissue/cell interface.

Step (vi) may include placing the at least polycaprolactone structure in a container with an excess amount of bioactive glass powder and agitating the container.

Advantageously, agitating the container will ensure an even and thorough coating of bioactive glass on the at least polycaprolactone structure.

Step (vi) may include dusting or blowing the at least polycaprolactone structure with heated bioactive glass powder.

Advantageously, as the heated bioactive glass powder may contact the surface of the at least polycaprolactone structure, it softens the at least polycaprolactone and firmly adheres to the surface. The at least polycaprolactone structure can be kept at room temperature or chilled before treatment.

Step (vi) may include liberally covering the at least polycaprolactone structure with bioactive glass powder and shaking off excess bioactive glass powder.

Advantageously, liberally covering the at least polycaprolactone structure with bioactive glass powder ensures a thorough coating of bioactive glass on the at least polycaprolactone structure.

The method of manufacturing may include a porous bioabsorbable composite scaffold further comprises the following step after step (vi):

heating the at least polycaprolactone structure to between 40 and 80° C. for between 5 and 15 minutes.

The at least polycaprolactone structure may be heated to about 58° C. for about 10 minutes.

Advantageously, heating the at least polycaprolactone structure softens the at least polycaprolactone and allows the bioactive glass to firmly adhere to the surface.

The method of manufacturing may include a porous bioabsorbable composite scaffold further comprises the following steps after step (v):

coating the at least polycaprolactone structure with a slurry comprised of an organic solvent, a polymer and bioactive glass particles; and allowing the slurry-coated at least polycaprolactone structure to dry.

Advantageously, coating the slurry onto the surface of the scaffold is another method of coating the scaffold with bioactive glass. Slurry coating also provides a relatively even and thorough coating of bioactive glass. The small amount of organic solvent softens the surface of the at least polycaprolactone structure and allow the bioactive glass particles to firmly adhere to the surface. The addition of a polymer assists the binding and dispersion of the glass coating. Furthermore, the slurry will partially infiltrate into the pores of the scaffold and deposit some bioactive glass within the scaffold.

The organic solvent may comprise at least one organic solvent from the following group of organic solvents:

(i) water, (ii) acetone, and (iii) ethanol.

Advantageously, acetone is found naturally in the body as a product of the metabolism of fats and is therefore not toxic to the body in trace amounts, unlike many organic solvents. Moreover, acetone is available at a relatively low cost compared to many other organic solvents. Ethanol has little or no harmful impact on the at least polycaprolactone structure.

The type or types of solvent used in the formulation of the slurry also depends on the type of polymer used in the slurry.

The polymer may comprise at least one polymer from the following group of polymers:

(i) polycaprolactone, (ii) polyvinyl alcohol, and (iii) polyvinyl butyral.

Advantageously, the polymers listed above are biocompatible. Polycaprolactone is soluble in acetone and polyvinyl alcohol is weakly soluble in ethanol and polyvinyl butyral is soluble in ethanol. The addition of a polymer allows the glass to adhere more readily to the surface of the at least polycaprolactone structure.

The method of manufacturing a porous bioabsorbable composite scaffold may further comprise the following step after step (i):

removing any undissolved solids from the at least polycaprolactone solution.

Advantageously, this step improves the accuracy in calculating the amount of polycaprolactone within each scaffold. Weighing the undissolved solids and comparing the result with the weight of the original amount of polycaprolactone added to the at least polycaprolactone solution enables the homogenous concentration of dissolved polycaprolactone to be calculated.

The method of manufacturing a porous bioabsorbable composite scaffold may further comprise the following steps prior to step (ii):

adding bioactive glass powder into the at least polycaprolactone solution, an mixing the at least polycaprolactone solution to form a substantially evenly mixed suspension of bioactive glass powder within the at least polycaprolactone solution.

Advantageously, this allows bioactive glass powder to be incorporated into the main structure of the scaffold, rather than coated on the surface of the scaffold, allowing the degradation rate and mechanical properties to be more easily controlled. Furthermore, degradation will be more stable and consistent.

According to a sixth aspect of the present invention, a method of increasing the density of a porous bioabsorbable composite scaffold is provided, comprising the following steps:

providing a porous bioabsorbable composite scaffold;

compressing the scaffold; and heating the scaffold for at least one second while compressed.

Advantageously, compressing the scaffold is a simple and effective method of increasing the density of the scaffold. Furthermore, this is a useful industrial processing method as compression is a process that can be reliably and consistently performed. Provided that the scaffolds provided are of consistent, known density, this process allows scaffolds in a range of different densities to be obtained from the same original scaffold manufacturing process.

According to a seventh aspect of the present invention, a method of joining two porous bioabsorbable composite scaffolds is provided, comprising the following steps:

providing two porous bioabsorbable composite scaffolds;

applying warm saline to a side of each of the scaffolds;

placing the moistened sides in contact with each other to form a join; and fixing the join with light contact pressure.

Advantageously, the application of warm saline having a temperature close to or at the melting temperature of polycaprolactone softens the surface of the polycaprolactone and facilitates bonding and joining. Furthermore, this procedure is relatively simple and can be performed as required just prior to implantation or in the laboratory as desired. For example, a scaffold structure larger than the size of a unit piece may be required to cover a large wound. In another example, an irregularly shaped scaffold may be created by joining several scaffolds together to cover irregularly shaped wounds.

According to an eighth aspect of the present invention, a method of manufacturing a porous bioabsorbable composite scaffold having graded porosity is provided, comprising the following steps:

(1) providing two or more porous bioabsorbable composite scaffolds, each of the scaffolds having a different density; and (2) joining the two or more scaffolds together.

Advantageously, this is a simple and effective method of forming a scaffold of graded porosity. Furthermore, providing the gradient in discrete layers allows the steepness of the gradient to be easily controlled as desired.

According to a ninth aspect of the present invention, a method of manufacturing a porous bioabsorbable composite scaffold having graded porosity comprising the following steps:

(1) providing three or more porous bioabsorbable composite scaffolds, each of the scaffolds having a different density; and (2) joining the three or more scaffolds together in order of increasing density.

Advantageously, this is a simple and effective method of forming a scaffold of graded porosity. Furthermore, providing the gradient in discrete layers allows the steepness of the gradient to be easily controlled as desired.

According to a tenth aspect of the present invention, a method of manufacturing a tissue repair system is provided, comprising the following steps:

applying warm saline to a first side of the first membrane layer and to a first side of the intermediate layer, placing the first side of the first membrane layer in contact with the first side of the intermediate layer to form a first join, fixing the first join with light contact pressure, applying warm saline to a first side of the second membrane layer and to a second side of the intermediate layer, placing the first side of the second membrane layer in contact with the second side of the intermediate layer to form a second join, and fixing the second join with light contact pressure.

Advantageously, the application of warm saline having a temperature close to or at the melting temperature of polycaprolactone softens the surface of the polycaprolactone and facilitates bonding and joining. Furthermore, this procedure is relatively simple and can be performed as required just prior to implantation or in the laboratory as desired.

In an aspect, there is provided a reinforced biocompatible scaffold for facilitating integration of biological tissue, the attachment device comprising:

a porous biocompatible scaffold;

at least one biocompatible filament and/or biocompatible conduit embedded within and fixed to the biocompatible scaffold.

In an aspect, there is provided a biocompatible composite scaffold for facilitating integration of biological tissue, the attachment device comprising:

a porous biocompatible scaffold;

an arrangement of at least one biocompatible filament and/or biocompatible conduit embedded within and fixed to the biocompatible scaffold.

The biocompatible scaffold may be functionally graded.

The biocompatible scaffold may be functionally graded by linearly varying density of the scaffold.

The biocompatible scaffold may have a hierarchical, interconnected porous structure.

The biocompatible scaffold may include a combination of macro-pores, micropores, and nano-pores.

The biocompatible scaffold may have a porosity that is 95% by volume.

The biocompatible scaffold may have a porosity within the range of 30 to 95% by volume.

The biocompatible scaffold may include bioactive glass. The bioactive glass may be 45S5 bioglass.

The biocompatible scaffold may include 5% by volume of bioactive glass.

The biocompatible scaffold may include proportion of bioglass of 20 wt %.

The proportion of bioglass within the biocompatible scaffold may be within the range of 0.1 wt %-35 wt %.

The proportion of biocompatible filament and/or biocompatible conduit within the biocompatible composite scaffold may be 0.05% of the total volume of the biocompatible composite scaffold. The proportion of biocompatible filament and/or biocompatible conduit within the biocompatible composite scaffold may be within the range of 0.01 to 50% of the total volume of the biocompatible composite scaffold.

The biocompatible scaffold may be configured to facilitate integration of soft tissue.

The biocompatible scaffold may be configured to facilitate integration of hard tissue.

The biocompatible scaffold may be mechanotransductive.

The biocompatible scaffold may be piezo active to mechanically stimulate cells to encourage cell proliferation and differentiation.

The at least one biocompatible filament and/or conduit may include 20 wt % of bioactive class.

In other embodiments, the at least one biocompatible filament and/or conduit may include bioactive glass.

The at least one biocompatible filament and/or conduit may be made of predominantly, polycaprolactone. The polycaprolactone may have a molecular weight corresponding to 80,000 measured using gel permeation chromatography.

The at least one biocompatible filament and/or conduit may include trace amounts of carbohydrate such as less than 1% of sucrose, glucose and fructose.

The at least one biocompatible filament may include 20 wt % of bioactive glass.

The at least one biocompatible filament may include a proportion of bioactive glass within the range of 0 to 30 wt %.

The diameter of the at least one biocompatible filament may be 20 μm.

In other embodiments, the diameter of the at least one biocompatible filament may be in the range of 1 to 50 μm). In other embodiments the diameter of the at least one biocompatible filament can be greater than 50 μm.

The at least one conduit may have an outer diameter of 1.2 mm and an inner diameter of 0.6 mm. In other embodiments the at least one conduit may have an outer diameter within the range of 0.5 mm to 1.7 mm. In other embodiments the at least one conduit may have an inner diameter within the range of 0.1 mm to 1.2 mm. In other embodiments the at least one conduit may have an inner diameter less than 0.1 mm or greater than 1.2 mm.

The at least one biocompatible filament and/or at least one biocompatible conduit may comprise a strain crystallised polymer.

The at least one biocompatible filament and/or at least one biocompatible conduit may comprise a strain crystallised polymer.

The at least one biocompatible filament and/or at least one biocompatible conduit may be substantially amorphous.

The at least one biocompatible filament may comprise light conductive material.

The at least one biocompatible filament may comprise bioglass.

The at least one biocompatible filament may comprise an arrangement of a plurality of filaments extending through an entire thickness of the biocompatible scaffold.

The at least one filament and/or conduit may have a substantially helical shape.

The at least one filament and/or conduit may be substantially straight and elongated.

The at least one biocompatible conduit may be made of semi-permeable material.

The at least one biocompatible conduit may comprise semi-permeable material to allow proliferation of cells, gases and other biological material through a wall of the conduit.

In an embodiment, the at least one filament may be oriented parallel to a surface of the cover within the biocompatible scaffold.

In another embodiment, the at least one filament perpendicularly to each of the inner surface and/or outer surface of the biocompatible scaffold.

In yet another embodiment, the at least one filament may be oriented at an angle to either the inner surface and/or the outer surface of the biocompatible scaffold layer.

The at least one biocompatible conduit may have a sealed end to retain a substance within the conduit. The substance may be a therapeutic substance such as a medicine.

The at least one filament and/or conduit may comprise an arrangement of a plurality of filaments and/or conduits.

The arrangement may be configured such that the stiffness of the biocompatible composite scaffold is under that of an average stiffness of bone.

The arrangement may be configured such that the stiffness of the biocompatible composite scaffold is under that of an average stiffness of cartilage.

The arrangement may be configured such that the stiffness of the biocompatible composite scaffold is under that of an average stiffness of soft tissue.

The arrangement may be configured such that the stiffness of the biocompatible composite scaffold is under that of an average stiffness of soft tissue.

In an aspect, there is provided a method of making a porous biocompatible scaffold comprising the steps of:

(i) providing solid polycaprolactone;

(ii) heating the solid polycaprolactone using a microwave until the solid polycaprolactone is translucent or substantially transparent;

(iii) mixing the heated polycaprolactone and organic solvent to providing a solution having a volume of polycaprolactone within the range of 10 to 50% of the total volume of the solution;

(iv) providing a porogen construct;

(v) immersing the porogen construct within the solution until the solution has sufficiently infiltrated the porogen construct;

(vi) coagulating the PCL within and around the porogen construct by immersing the porogen construct within the solution in water.

The solid pcl may have a molecular weight corresponding to 80,0000 measured using gel permeation chromatography.

The organic solvent may be acetone.

The method may further include:

heating the porogen construct immersed in solution in a microwave before coagulating the PCL within and around the porogen construct.

Coagulating the PCL within and around the porogen construct by immersing the porogen construct within the solution in water.

removing any skins formed on surfaces of the porogen during coagulation to facilitate diffusion of acetone, water and sucrose within the solution The method may further include:

(vii) heating the coagulated scaffold in a microwave at a temperature just under the melting temperature of the scaffold such that the outer surfaces of the scaffold are softened;

(viii) coating the coagulated PCL with bioactive glass powder.

The bioactive glass powder can have a diameter within the range of 10 to 15 μm.

Immersing the porogen construct within the solution may include agitating the porogen construct within the solution until the solution sufficiently infiltrates the porogen construct.

The method may further include the steps of:

adding an acetone solution to the polycaprolactone to form a polycaprolactone-acetone solution mixture after heating the scaffold masticating the polycaprolactone-acetone solution mixture before step Masticating may include placing the polycaprolactone-acetone solution mixture in a bag made of Low density polyethylene (or LDPE) and applying a rolling press to the bag. In this way, no bacteria or other undesirable foreign material will not be introduced into the polycaprolactone-acetone solution mixture.

The method may further include:

(1) (ix) dissolving and washing out the porogen material and organic solvent from the coagulated scaffold to substantially remove the porogen material and organic solvent.

(2) (x) drying the scaffold.

In another aspect, there is provided a method of making a biocompatible filament or a biocompatible conduit, comprising:

(1) making a precursor composition including polycaprolactone;

(2) heating the precursor composition to form a molten mixture;

(i) adding powdered bioactive glass (ii) masticating the molten mixture to eliminate any agglomerates to ensure even distribution of powder throughout the mixture;

(iii) forming the molten mixture into a rod to draw a filament or forming the molten mixture into a hollow cylinder to draw a conduit;

(iv) adjusting the temperature of the precursor material to a desired temperature for drawing, (3) drawing a filament or conduit from the precursor material.

Making a precursor material including polycaprolactone may include providing a biocompatible scaffold comprising polycaprolactone.

In another aspect, there is provided a method of making a biocompatible filament or a biocompatible conduit, comprising:

(1) making a precursor material using the steps of:

(i) providing a coagulated biocompatible scaffold using the following method of making a porous biocompatible scaffold comprising, the steps of:

(i) providing solid polycaprolactone;

(ii) heating the solid polycaprolactone using a microwave until the solid polycaprolactone is translucent or substantially transparent;

(iii) mixing the heated polycaprolactone and organic solvent to providing a solution having a volume of polycaprolactone within the range of 10 to 50% of the total volume of the solution;

(iv) providing a porogen construct;

(v) immersing the porogen construct within the solution until the solution has sufficiently infiltrated the porogen construct;

(vi) coagulating the pcl-acetone solution mixture within and around the porogen construct by immersing the porogen construct within the solution in water;

(vii) heating the coagulated scaffold in a microwave at a temperature just under the melting temperature of the scaffold such that the outer surfaces of the scaffold are softened;

(viii) coating the coagulated PCL scaffold with bioactive glass powder; heating the coated scaffold mixture including bioactive glass powder to form a molten mixture;

(ix) masticating the molten mixture to eliminate any agglomerates to ensure even distribution of powder throughout the mixture;

(x) forming the molten mixture into a rod to draw a filament or forming the molten mixture into a hollow cylinder to draw a conduit;

adjusting the temperature of the rod or hollow cylinder to a desired temperature for drawing, drawing a filament or conduit from the precursor material.

Filament and/or conduits may be drawn using a conventional drawing process suitable for drawing plastics into thread or filaments.

In another embodiment, filaments may be drawn using an electrospinning process to produce filaments with a diameter within the nano range.

Drawing a filament or conduit from the precursor material may comprise:

heating the rod or cylinder at a drawing temperature clamping a first end of the rod or hollow cylinder fastening a second end of the rod to a rotatable spool rotating the spool.

To draw a predominantly amorphous filament or conduit the drawing temperature may be in the range of 60 to 95 degrees Celsius and a drawing rate of within the range of 1 to 15 mm per second.

The filament or conduit can be drawn at a rate of 10 mm/second at a temperature at approximately 80 degrees Celsius.

To draw a predominantly strain crystallised filament or conduit, the drawing rate may be within the range 15 to 500 mm/second and at a temperature within the range of 0 to 58 degrees.

For example, to achieve a strain crystallised filament or conduit, the filament or conduit can be drawn at 20 degrees Celsius at a rate of 20 mm/s.

In another embodiment, biocompatible filaments or conduits can be formed via electrospinning.

In another aspect of the attachment device, there is provided a method of making an attachment device for connecting a medical device to the tissue of a subject, comprising:

(1) providing a biocompatible scaffold configured to facilitate biological tissue integration within the scaffold;

(2) providing a plurality of biocompatible filaments and/or at least one biocompatible conduit;

(3) embedding the plurality of biocompatible filaments within the biocompatible scaffold;

(4) fusing each filament to the scaffold to fix each filament within the scaffold.

At least one of the plurality of biocompatible filaments and/or at least one biocompatible conduit may be helical.

(1) Embedding the at least one biocompatible filament may comprise:

(i) providing a helical wire substantially identical in shape and size to a helical filament of the at least one biocompatible filament;

(ii) the helical wire having a first end and a second end;

(iii) attaching one end of a helical biocompatible filament to the second end of the helical wire;

(iv) rotatably inserting the helical wire into the scaffold to create a helical channel to house the biocompatible filament within the scaffold;

(v) removing the helical wire from the scaffold by continuing to rotate the helical wire through the scaffold until the path is filled with the biocompatible filament and the helical wire is out of the scaffold;

(vi) detaching the helical wire from the biocompatible filament.

In another embodiment, embedding the at least one biocompatible filament may comprise threading one or more of the at least one biocompatible filament or conduit through the scaffold using a sewing needle.

Fusing each filament to the scaffold to fix each filament within the scaffold may include solvent welding using an acetone solution.

Fusing each filament to the scaffold to fix each filament within the scaffold may include solvent welding using a solution comprising acetone and polycaprolactone.

Fusing each filament or conduit to the scaffold to fix each filament or conduit within the scaffold may include gently spot welding the filament by contacting each filament using water at a temperature within the range of 60 degrees Celsius to 70 degrees Celsius.

Fusing each filament to the scaffold to fix each filament within the scaffold may include gently spot welding each filament by selectively applying water at a temperature within the range of 58 degrees Celsius to 72 degrees Celsius to the filament.

In yet another embodiment, there is provided a method of embedding comprising:

(1) providing a biocompatible scaffold;

(2) providing an arrangement of cannulated needles, each needle having an internal channel;

(3) inserting a biocompatible filament or biocompatible conduit into the internal channel of each needle;

(4) inserting the arrangement of cannulated needles at least partially into the scaffold to create voids within the scaffold to house each filament;

(5) moving each cannulated relative to each filament to removing each cannulated needle from the scaffold; and (6) fixing the biocompatible filaments to the biocompatible scaffold.

The at least one filament and/or conduit can be fused to the scaffold by heating the composite scaffold to a temperature within the range of 58 degrees Celsius to 60 degrees Celsius for approximately three to five minutes.

The at least one filament and/or conduit may be fused to the scaffold by placing the scaffold with the embedded filament and/or conduit in contact with water at a temperature within the range of 60 degrees Celsius to 70 degrees Celsius.

The at least one biocompatible conduit may have a sealed end to retain a substance within the conduit. The substance may be a therapeutic substance such as a medicine.

The at least one biocompatible conduit may be semipermeable to allow movement of cells and biological material through the conduit.

The at least one biocompatible conduit may be made of semi-permeable material to allow medicine to slowly leach out of the semi-permeable material. Upon gradual bioresorption of the conduit, the medicine may be released into surrounding biological tissue.

Other aspects of the invention are also disclosed.

BRIEF DESCRIPTION OF THE DRAWINGS

Notwithstanding any other forms which may fall within the scope of the present invention, embodiments of the invention will now be described, by way of example only, with reference to the accompanying drawings in which.

DETAILED DESCRIPTION OF SPECIFIC EMBODIMENTS

Figure 1:
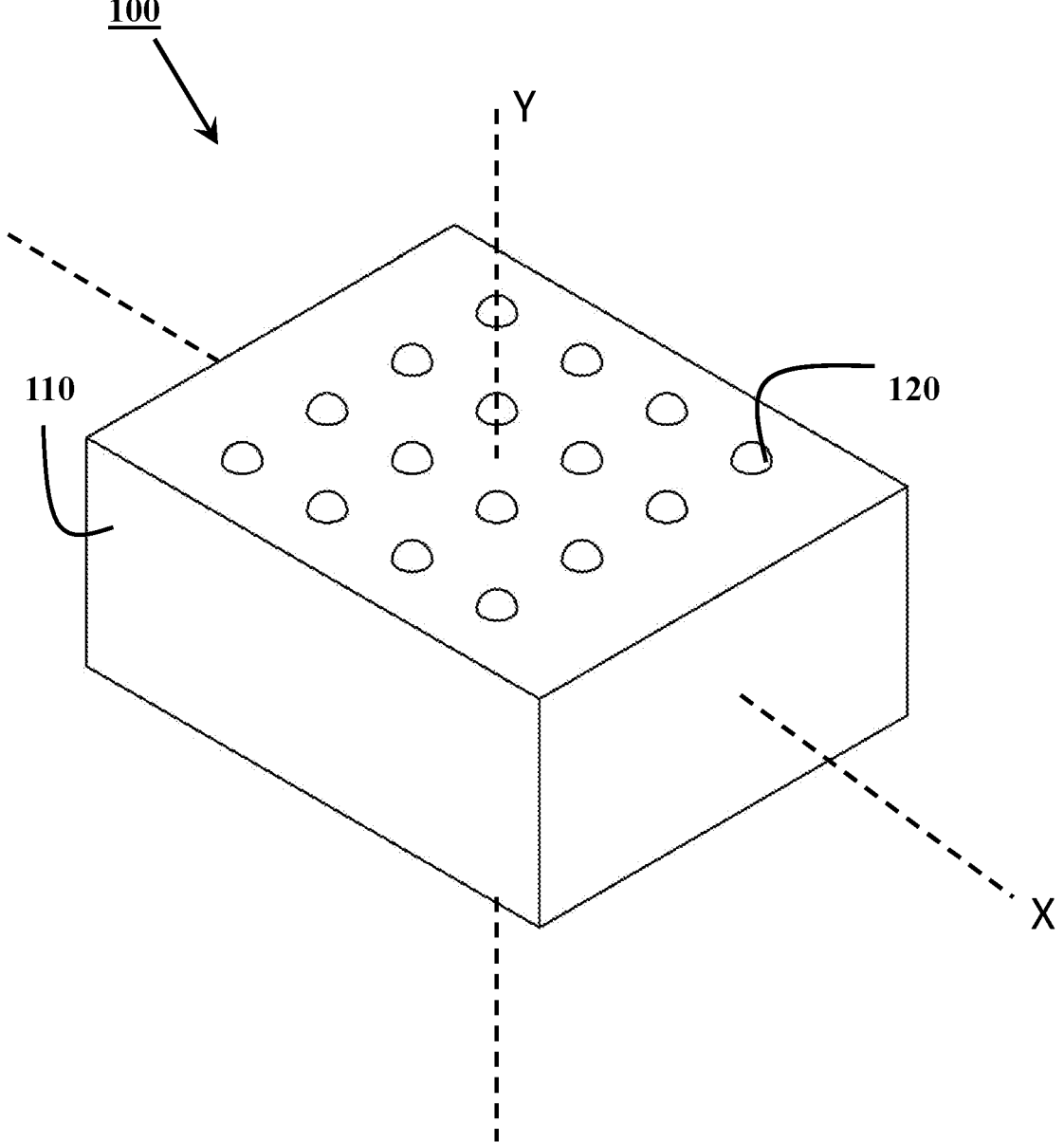
FIG. 1 is a schematic of a reinforced biocompatible scaffold in accordance with an embodiment of the present invention.

According to a first embodiment of the present invention, a porous bioabsorbable composite scaffold is provided, comprising a polymeric component and one or more bioactive components and having a generally random arrangement of struts defining an interconnected network of pores. In one embodiment, the scaffold is also tissue conductive.

The scaffold is suitable for use in laboratory and clinical applications such as cell culture, tissue engineering, fracture and wound healing and defect filling. The generally random arrangement of struts in the scaffold significantly contributes to the ability of the scaffold to support substantial compressive, shear and rotational strain along different orthogonal and non-orthogonal axes with proportional increments in stress. On the other hand, in comparison, a mesh or periodically repeating array of strut connections is more susceptible to buckling instability when subjected to substantial compressive, shear or rotational strain along different orthogonal and non-orthogonal axes with proportional increments in stress.

The addition of one or more bioactive components to the scaffold has a number of distinct advantages. Firstly, provides or enhances the bioactivity of the scaffold. Secondly, it allows the degradation rate and the mechanical properties of the scaffold to be customised. This can be easily achieved by varying the relative amounts of the polymeric and bioactive components. Furthermore, the addition of a bioactive component alters the physical structure of the scaffold, which changes the degradation behaviour and mechanical properties of the scaffold. The elastic modulus of the scaffold can be customised to generally match or be slightly stiffer than the modulus of soft tissue.

In one embodiment, the polymeric component is polycaprolactone. In another embodiment, the polymeric component is polycaprolactone combined with one or more polymer modifiers, for example, polylactic acid or polyvinyl pyrrolidone.

It is advantageous that the scaffold has a polymeric component as polymers are relatively tough, compressible and elongatable and easily processable due to their relatively low glass transition temperatures and melting temperatures. More specifically, the use of polycaprolactone (PCL) is advantageous, as it is widely regarded as a bioabsorbable and soft and hard tissue compatible material. As with many polymers, its low melting point and glass transition temperature makes it easily processable. In comparison to other polymers that are used in similar applications, such as polyglycolide (PLGA), poly(DL-lactide) (DL-PLA), poly (L-lactide) (L-PLA) and polyglycolic acid (PGA), the relatively lower melting point of polycaprolactone of 58-63° C. allows it to be processed at temperatures that are easily achievable in a common laboratory or clinical setting. Additionally, PCL has a relatively low elastic modulus of 0.21-0.34 MPa, which is comparable to the elastic modulus of human skin, which is 0.2-3 MPa. This parity makes it very suitable for use as a component in a soft tissue scaffold as it reduces or eliminates the amount of trauma caused to neighbouring soft tissues. A low elastic modulus also reduces or eliminates the phenomenon of stress shielding in bone. Furthermore, PCL is able to achieve large elongations before fracturing while withstanding substantial shear and tensile forces. Therefore, PCL is a tough material. Skin grafts are often subjected to such forces and thus PCL is suitable for synthetic skin replacement and grafting. Polycaprolactone also has a relatively low rate of degradation, allowing more stable resorption and wound healing as it elicits milder inflammatory responses and foreign body reactions in comparison to materials that have faster rates of degradation.

Advantageously, introducing polymer modifiers enables the main polymer to be modified to produce a more desirable degradation profile. In particular, modified polymers are generally stronger and have higher elastic moduli. Thus, the polymeric component of the scaffold will be stronger and have a higher elastic modulus if made of polycaprolactone combined with one or more polymer modifiers.

In one embodiment, the pore structure is relatively regular in distribution and comprises macropores, mesopores and nanopores.

It is highly desirable for a range of pore sizes, ranging from macropores to nanopores, to be present in the interconnected porous structure of the scaffold. Macropores help govern scaffold mechanical properties and tissue architecture and vascularisation, and promote the infiltration of cells, vessels and connective tissue into the scaffold. Mesopores and nanopores affect the surface energy of the cell interfaces of the scaffold (which, in turn affects the wetting, adsorption, degradation, ion release and buffering properties) impacting on the function, attachment, proliferation and migration of cells into the scaffold.

In another embodiment, the porous bioabsorbable composite scaffold has a graded porosity. The porosity of the scaffold can be graded to various extents. In one embodiment, the porosity is graded linearly through the scaffold.

Advantageously, modifying the porosity of the scaffold affects its degradation rate and mechanical properties. For in vivo applications, providing a scaffold of graded porosity supports tissue transitions, that is, if the scaffold is used to interface different types of tissue to either side of it. In one example, the scaffold may be used to interface derma to one side and subcutaneous tissue or fat to the other side. In another example, the scaffold may be used to interface cartilage to one side, and bone to the other side. In another example, the scaffold may be used to interface tendon to one side and bone to the other side. For in vitro applications, a scaffold of graded porosity is useful in cell culture to determine optimum porosities for particular cell types.

In one embodiment, at least one of the one or more bioactive components is coated on the polymeric component. Providing the one or more bioactive components as a coating is advantageous as this locates the bioactivity directly at the cell interface.

In another embodiment, at least one of the one or more bioactive components is incorporated within the polymeric component. Advantageously, the degradation rate and mechanical properties are easily controlled and are stable over a relatively extended period of time during degradation. This allows the scaffold to retain its bioactivity during the healing process. The at least one of the one or more bioactive components can take the form of a nano, mesa or micro particle or fibre.

In one embodiment, at least one of the one or more bioactive components is substantially regular in distribution throughout the scaffold, however, in another embodiment the relative amount of the at least one of the one or more bioactive components is graded within the polymeric component.

Grading the relative amounts of bioactive components allows the bioactivity, degradation rate and mechanical properties of the scaffold to be graded through the scaffold. This is desirable if, for example, the scaffold is used to interface different types of tissue to either side of it. In one embodiment, at least one of the one or more bioactive components is a powdered bioactive glass, comprising micro and nano particulates or fibres. In one embodiment, the bioactive glass is in solid form, and in another embodiment, the bioactive glass is in mesoporous form. In another embodiment, the bioactive glass is coated with a therapeutic substance, such as a bone morphogenic protein (BMP).

Advantageously, bioactive glass powder is readily coated on and incorporated into polymer structures using techniques such as dry-pressing or slurry coating. Coating or incorporating bioactive glass into the scaffold provides or improves the soft and hard tissue bonding capabilities of the scaffold.

In another embodiment, at least one of the one or more bioactive components is hydroxyapatite. Hydroxyapatite is bioactive and particularly improves the hard tissue bonding capabilities of the scaffold. It also has relative low rate of degradation in comparison to bioactive glass and thus may be advantageous for bone binding applications, for example, fracture healing.

Another advantage of providing a bioactive glass component is the ability of bioactive glass to buffer the acidic environment produced by polymer degradation products, thereby reducing the hostility of the wound or defect environment. Furthermore, bioactive glass has a relatively high degradation rate. Thus, coating or incorporating varying amounts of a bioactive glass phase into the scaffold allows the degradation rate of the scaffold to be customised. Adding bioactive glass in relatively small particles provides a large reactive surface area for enhanced bioactivity.

Bone morphogenic proteins assists with hard and soft tissue repair and can be advantageously introduced into the scaffold as a coating on a bioactive glass component as they readily adhere to the hydrated surface layers that form on bioactive glasses in use.

In another embodiment, at least one of the one or more bioactive components is sugar, caramelised sucrose, an antibiotic or a plurality of antibiotics, a growth factor or a combination of a plurality of growth factors, a bioactive honey or a wax derived from a honey.

Advantageously, sugar and caramelised sucrose can be broken down and used by cells as an energy source. When placed in contact with cells, sugar and caramelised sucrose help regulate the biological functions and the quality and quantity of cell-to-cell interaction. Additionally, caramelised sucrose has antibacterial properties.

Advantageously, antibiotics kill or inhibit the growth of bacteria. If the scaffold is used in a wound healing or defect filling application, this prevents the wound or defect from becoming infected, which prevents or slows healing. Growth factors stimulate cellular growth, proliferation and cellular differentiation by regulating a variety of cellular processes. Bioactive honey (medihoney) may be used to assist with the dermal wound healing properties of the scaffold. Honey also has antibacterial properties stemming from its relatively low pH of 3.2 to 4.5, and thus it prevents and inhibits the growth of microorganisms. Honey also assists tissue repair due to its hyperosmolarity and stimulating of body enzymes, which promotes the removal of necrotic tissue in the wound. Furthermore, honey releases hydrogen peroxide, which promotes the formation of new blood vessels and fibroblast, thus increasing the rate at which granulation tissue is created.

In one embodiment, the porous bioabsorbable composite scaffold further comprises one or more additive components.

Advantageously, providing one or more additive components improves the properties, functionality and/or versatility of the scaffold.

In one embodiment, at least one of the one or more additive components is a radio-opaque component such as barium sulphate particles or barium-modified bioactive glass particles.

Advantageously, this allows the form and position of the scaffold to be monitored using x-ray during and following implantation. Barium sulphate is a widely accepted, clinically used radiocontrast agent that, in small amounts, has little to no harmful impact on the body. Low amounts of barium in bioactive glass increases the radio-opacity of bioactive glass and also has little to no harmful impact on the body.

In another embodiment, at least one of the one or more additive components is a magnetic component, such as pure iron particles, ferrous oxide particles or ferric oxide particles.

Advantageously, the addition of a magnetic component allows the scaffold to be actuated and vibrated using an externally applied magnetic field. This is useful for in vitro mechanical actuation. Moreover, mechanical movement of the scaffold in vivo stimulates the surrounding tissue, which enhances wound healing. Moving the scaffold may also provide a pumping action which assists the removal of neutrophils (pus) from the wound site, thereby accelerating the rate of healing. Pure iron particles, ferrous (II) oxide particles and ferric (III) oxide particles are magnetic and are biocompatible.

In yet another embodiment, at least one of the one or more additive components is an electrically conductive component, such as magnesium based glass particles, iron based glass particles or calcium based glass particles.

Advantageously, addition of an electrically conductive component allows electrical charge to be evenly dispersed within the scaffold when used as an electrode base for muscle actuation. This is useful in vascular and functional electrical stimulation (FES) applications.

Magnesium glass particles, iron glass particles and calcium glass particles are electrically conductive and are biocompatible.

In another embodiment, at least one of the one or more additive components is a piezoelectric component, such as a piezoelectric crystal, a piezoelectric polymer, a piezoelectric ceramic, a lead-free piezoelectric ceramic (e.g. magnesium glass, iron glass or calcium glass).

Advantageously, addition of a piezoelectric component causes the scaffold to produce a slight potential difference when mechanically strained. This allows the scaffold to act as a sensor for strain and mechanical manipulation in vivo, facilitating its use as a diagnostic device for monitoring fracture or wound healing processes. Magnesium glass, iron glass and calcium glass are piezoelectric, electrically conductive and are biocompatible.

In one embodiment, at least one of the one or more additive components is a biocompatible polymer-coated magnetic component, such as biocompatible polymer-coated ferrous oxide particles or biocompatible polymer-coated ferric oxide particles. In another embodiment, at least one of the one or more additive components is a biocompatible glass-coated magnetic component such as biocompatible glass-coated ferrous oxide particles or biocompatible glass-coated ferric,111) oxide particles. In another embodiment at least one of the one or more additive components is biocompatible silicon-coated magnetic component, such as biocompatible silicon-coated ferrous oxide particles or biocompatible silicon-coated ferric oxide particles.

Advantageously, the addition of a biocompatible polymer-coated, glass-coated or silicon-coated magnetic component imparts similar advantages to the addition of a magnetic component, as described above. In addition to this, mechanically actuating the biocompatible polymer-coated, glass-coated or silicon-coated magnetic component facilitates the degradation of the scaffold at an accelerated rate. For example, this can be achieved by subjecting the scaffold to an oscillating remote magnetic field. Ferrous oxide particles and ferric oxide particles are magnetic and are biocompatible.

Moreover, coating magnetic particles with polymer, glass or silicon prevents or retards the degradation of the magnetic particles, thus extending the longevity of the magnetic functionality of the scaffold. It also isolates the magnetic particles from tissues when the scaffold is in use. For example, despite the biocompatibility and relatively slow degradation rate of pure iron particles, ferrous,11) oxide particles and ferric,111i oxide particles, it is still desirable in some instances to prevent direct contact between the particles and tissues, especially in in vitro culture and tissue engineering applications. The depending on the specific composition used, the coating can be stable to prevent degradation or dissolvable to still allow the disappearance of foreign particles within the body over time.

In another embodiment, at least one of the one or more additive components is a biocompatible polymer-coated electrically conductive component, such as biocompatible polymer-coated iron particles, biocompatible polymer-coated calcium particles or biocompatible polymer-coated magnesium particles. In another embodiment, at least one of the one or more additive components is a biocompatible glass-coated electrically conductive component, such as biocompatible glass-coated iron particles, biocompatible glass-coated calcium particles or biocompatible glass-coated magnesium particles. In another embodiment, at least one of the one or more additive components is a biocompatible silicon-coated electrically conductive component, such as biocompatible silicon-coated iron particles, biocompatible silicon-coated calcium particles or biocompatible silicon-coated magnesium particles.

Advantageously, the addition of a biocompatible polymer-coated, glass-coated or silicon-coated electrically conductive component imparts similar advantages to the addition of an electrically conductive component, as described above. In addition to this, mechanically actuating and/or inducing a potential difference in the biocompatible polymer-coated, glass-coated or silicon-coated electrically conductive component facilitates the degradation of the scaffold at an accelerated rate. For example, this can be achieved by subjecting the scaffold to an oscillating remote magnetic field. Moreover, coating electrically conductive particles with polymer, glass or silicon prevents or retards the degradation of the electrically conductive particles, thus extending the longevity of the electrically conductive functionality of the scaffold. It also isolates the electrically conductive particles from tissues when the scaffold is in use. For example, despite the biocompatibility of iron, calcium and magnesium particles, it is still desirable in some instances to prevent direct contact between the particles and tissues, especially in in vitro culture and tissue engineering applications. The depending on the specific composition used, the coating can be stable to prevent degradation or dissolvable to still allow the disappearance of foreign particles within the body over time.

Advantageously, iron particles, calcium particles and magnesium particles are electrically conductive and are biocompatible. In one embodiment, the scaffold is adapted to be sterilised by ultraviolet or gamma irradiation.

Advantageously, sterilisation is required in order to prevent the introduction of foreign microorganisms within the scaffold in vitro or in vivo. Furthermore, exposing polymers to ultraviolet or gamma radiation affects the degradation rate of the polymer in biological fluids, depending on the radiation dosage and type. Exposure to radiation has also been shown to affect the elastic modulus of the exposed polymer. These effects allow the use of radiation to have a dual purpose. The first is sterilisation of the scaffold, and the second is the manipulation or customisation of the physical properties of the polymeric component of the scaffold. In addition to this, exposing polycaprolactone with gamma rays causes it to cross-link. The extent of cross-linking, and thus the associated mechanical properties of the scaffold, can be controlled by manipulating the dosage of the gamma radiation.

In one embodiment, the scaffold further comprises a soluble, structurally supportive, temporary filler component adapted to prevent deformation of the scaffold during transport, delivery and/or implantation. For example, the soluble structurally supportive temporary filler component is a sugar or a dehydrated hydrogel or hydrocolloid component that is adapted to increase in volume when hydrated.

Advantageously, providing a temporary filler component prevents damage to the scaffold during transport, delivery and implantation by helping maintain the structure and shape of the scaffold. Sugar is a good material to use as a temporary filler as it is stiff and will provide good structural support to the scaffold. Furthermore, sugar is capable of dissolving in vivo and can deliver bioactive molecules or proteins. A dehydrated hydrogel or hydrocolloid component will also prevent deformation of the scaffold during transport, delivery and/or implantation, which prevents it from being damaged.

In one embodiment, the scaffold is adapted to be compressed and expands when the dehydrated hydrogel or hydrocolloid is hydrated.

A pre-compressed or pre-shrunk scaffold will be more easily implanted and positioned in vivo. The scaffold will expand on exposure to the biological fluids to fill defects or fractures or close wounds as it is hydrated, leading to a reduced chance of collapse and expulsion from the defect, fracture or wound.

In one embodiment, the porous bioabsorbable composite scaffold is adapted to absorb an in vivo additive component delivered in vivo subsequent to the implantation of the porous bioabsorbable scaffold. Examples of components that may be delivered in vivo are a hydrogel a protein, cells, a tissue or stem cells.

Advantageously, additive components, such as donor cells or tissues, therapeutic substances or bioactive substances, may be delivered to directly to the implant site to accelerate healing. This is particularly useful if continual delivery of additive components is desired or required, for example, regular courses of antibiotics, or if bioactive components quickly degrade and need to be replenished.

Advantageously, delivering bioactive components such as hydrogels and proteins help promote the differentiation, attachment and/or proliferation of cells at the fracture, defect or wound site. Delivering additive components in vivo such as cells, tissues and stem cells helps replenish the cell stock at the site. Furthermore, being able to deliver additive component post-implantation allows the substances to be replenished as desired.

According to another embodiment of the present invention, a bioabsorbable pump is provided, comprising a porous bioabsorbable composite scaffold as previously described. The bioabsorbable pump further comprises an outer membrane covering the scaffold, an inlet located through the outer membrane having a first unidirectional valve, and an outlet located through the outer membrane having a second unidirectional valve, the first unidirectional valve being adapted to allow fluid to enter the scaffold and the second unidirectional valve being adapted to allow fluid to exit the scaffold when the pressure within the scaffold exceeds a threshold value. In one embodiment, the first and second unidirectional valves take the form of leaflet valves.

Advantageously, the pump facilitates the perfusion of biological fluids and nutrients through and the removal of waste from an area, such as in the intervertebral disc. This is particularly beneficial for areas with reduced capacity for biological fluids, nutrient and waste cycling, due to damage or disease. On the other hand, enhancing such bodily functions allows wound, fracture or defect healing to be accelerated. In an in vitro application, the pump can be used as a bioreactor, supporting a biologically active environment and simulating in vivo conditions. Leaflet valves have a simple mechanical design and cause relatively little or no damage to cells, making it particularly suitable for use in the body.

In one embodiment, the pressure within the scaffold may be increased to the threshold value by subjecting the bioabsorbable pump to a compressive force.

In this embodiment, the pump can be activated by a simple mechanical action. This mechanical action may be deliverable by the natural body movement of the individual in whom the scaffold is implanted. This compressive force may also be supplied by a simple mechanical actuator for ex vivo applications.

In another embodiment, the pressure within the scaffold may be increased to the threshold value by applying a magnetic field or an electromagnetic field.

In this embodiment, the pump is able to be actuated magnetically or electromagnetically.

Thus, the pump maybe activated by external, remote means, which may be desirable if it has been implanted in the body.

In one embodiment, the outer membrane is substantially made of a polymer.

Advantageously, polymers are relatively tough, compressible and elongatable and easily processable due to their relatively low glass transition temperatures and melting temperatures.

In another embodiment, the outer membrane is substantially made of a polymeric composite.

Advantageously, the use of a polymeric composite allows the physical, mechanical and biochemical properties of the scaffold to be more customisable and controllable.

According to another embodiment of the present invention, a tissue repair system is provided, comprising a first membrane layer, a second membrane layer, and an intermediate layer. The intermediate layer joined to and located intermediate the first and second membrane layers and is made substantially of a porous bioabsorbable composite scaffold as previously described. The first and second membrane layers of the tissue repair system can be customised in terms of permeability, elastic modulus and strength for specific applications. For example, differentiating the properties of the first and second membrane layers allow the tissue repair system to better support tissue transitions, e.g. derma to fat transitions or connective tissue to bone transitions.

In one embodiment, the first membrane layer is an elastic semi-permeable membrane and the second membrane layer is a permeable membrane. In this embodiment, the first membrane layer is suitable for use as an outer layer for a synthetic skin graft, allowing gas exchange and a small amount of moisture loss, but preventing infection and wound breach. The second membrane layer is suitable for interfacing with internal tissues, such as organs, connective/vascular tissues or bone. This embodiment is particularly suited for a derma to fat transition.

In another embodiment, the first membrane layer is an elastic semi-permeable membrane and the second membrane layer is also a semi-permeable membrane. This tissue repair system is more suitable for closing or repairing a surface wound.

In one embodiment, the first and/or second membrane layers are made from a polymer, such as polycaprolactone.

Advantageously, polymers are relatively tough, compressible and elongatable and easily processable due to their relatively low glass transition temperatures and melting temperatures. Polycaprolactone (PCL) is a bioabsorbable and soft and hard tissue compatible material, with a low melting point and glass transition temperature, a relatively low elastic modulus, a high ductility and a relatively low rate of degradation.

In another embodiment, the first and/or second membrane layer, in the form of semi-permeable membranes, are made from a polymeric composite, for example, a polycaprolactone-bioactive-glass composite comprising bioactive glass in the form of nano-particulates.

Advantageously, the use of a polymeric composite allows the physical, mechanical and biochemical properties of the membrane layer to be more customisable and controllable. Coating or incorporating bioactive glass into the membrane layer provides or improves the soft and hard tissue bonding capabilities of the membrane layer.

Furthermore, the degradation of the bioactive glass serves to buffer the acidic environment caused by polymer degradation products. Adding bioactive glass in relatively small particles provides a large reactive surface area for enhanced bioactivity.

In another embodiment, the second membrane layer, in the form of a permeable membrane, is made from a polymeric composite, for example, a polycaprolactone-bioactive-glass composite comprising bioactive glass in the form of bioactive glass fibres.

Advantageously, reinforcing a polymer membrane with bioactive glass fibres improves the tensile modulus and strength of the membrane.

According to another aspect of the present invention, a tissue repair system is provided, comprising a core and a sheath enclosing the core. In this embodiment, the core is made substantially of a porous bioabsorbable composite scaffold as previously described and the sheath is substantially made of an elastic semi-permeable membrane.

Advantageously, the tissue repair system can be used for closing or repairing a surface wound, allowing gas exchange and a small amount of moisture loss, but preventing infection and wound breach.

According to another embodiment of the present invention, a method of manufacturing a porous bioabsorbable composite scaffold is provided, comprising the following steps:

(1) (xi) dissolving at least polycaprolactone in an organic solvent to form an at least polycaprolactone solution;

(2) (xii) immersing a porogen construct in the at least polycaprolactone solution to form a temporary composite comprising at least organic solvent, porogen material and a polycaprolactone structure; and (3) (xiii) removing the temporary composite from the at least polycaprolactone solution.

Advantageously, dissolving at least polycaprolactone (PCL) in an organic solvent and immersing the porogen construct in the at least polycaprolactone solution facilitates the infiltration of polycaprolactone into the interstices of the porogen construct. The porogen construct provides a template or a negative mould for the scaffold.

In one embodiment, the organic solvent is acetone.

Advantageously, acetone is found naturally in the body as a product of the metabolism of fats and is therefore not toxic to the body in trace amounts, unlike many organic solvents.

Moreover, acetone is available at a relatively low cost compared to many other organic solvents.

In one embodiment, the porogen construct is a sugar construct, comprised of at least sucrose, glucose, fructose, galactose, or casein.

Advantageously, the sugar construct is able to be provided having an interconnected network of pores with a high degree of porosity and substantially random arrangement of struts for support, making it suitable as a template for the scaffold. Furthermore, sugar is a biocompatible and bioactive material, and thus allowing the sugar to remain either in bulk or in trace amounts is not detrimental to and may enhance cellular growth and proliferation. Sugar also advantageously provides nutrition for cells and limits bacterial growth, and thus will accelerate the wound healing capabilities of the scaffold. Advantageously, the sugars listed above are naturally occurring sugars found in the body.

In another embodiment, the porogen construct is a salt construct, comprised of at least one of sodium chloride, calcium phosphate, and monosodium glutamate.

Advantageously, the salt construct is able to be provided having an interconnected network of pores with a high degree of porosity and substantially random arrangement of struts for support, making it suitable as a template for the scaffold. Furthermore, use of biocompatible salts are not detrimental to and may enhance cellular growth and proliferation.

Advantageously, the salts listed above are naturally occurring salts and provide nutrition for wound healing. In particular, calcium phosphate forms an anisotropic solid having needle-like formations and monosodium glutamate (MSG) forms an anisotropic solid having rod-like formations. Thus, scaffolds formed from a calcium phosphate or monosodium glutamate constructs will also be anisotropic, which can be advantageous for providing directionality. Depending on the porogen used, scaffolds of differing connective strut arrays can be manufactured. Monosodium glutamate has also been shown to have neural stimulative properties.

In one embodiment, the method of manufacturing a porous bioabsorbable composite scaffold further comprises the step of:

(1) (xiv) removing an outer membrane from the temporary composite to leave an at least polycaprolactone structure.

The membrane is a layer of residual polycaprolactone that is removed to advantageously facilitate further scaffold processing.

In another embodiment, the method of manufacturing a porous bioabsorbable composite scaffold further comprises the following step:

(1) (xv) drying the scaffold.

In one embodiment, step (v) includes centrifuging the at least polycaprolactone structure and blowing the at least polycaprolactone structure with clean, filtered air.

Advantageously, drying the scaffold in clean, filtered air prevents or reduces the introduction of contaminants into the polycaprolactone structure and is an effective and cost-effective method of drying the scaffold. In one example, the air can be cleaned and filtered using a HEPA filter. The at least polycaprolactone structure can then be transported, delivered and implanted without removal of the porogen material. The stiffness of the porogen material prevents deformation of the structure and can be removed prior to implantation or implanted as it is.

In another embodiment, the method of manufacturing a porous bioabsorbable composite scaffold further comprises the following additional step prior to step (v):

(1) dissolving and washing out the porogen material and organic solvent from within the temporary composite to substantially remove the porogen material and organic solvent from the at least polycaprolactone structure.

Advantageously, the porogen material and organic solvent can be removed, allowing the at least polycaprolactone structure to be used as a porous bioabsorbable scaffold.

In one embodiment, the additional step includes washing the at least polycaprolactone structure in circulating water.

Advantageously, removing the porogen material and organic solvent comprises a simple step of washing it under circulating water, for example under running water, which can be easily performed in the laboratory.

In one embodiment, the at least polycaprolactone structure is washed in circulating water for at least 30 minutes, 1 hour or 12 hours.

Advantageously, washing the at least polycaprolactone structure under circulating water for an extended period of time ensures the removal of all or at least a substantial portion of the porogen material and organic solvent.

In one embodiment, the additional step includes soaking the temporary at least polycaprolactone structure in a water bath and rinsing repeatedly.

Advantageously, soaking the at least polycaprolactone structure ensures that all or at least a substantial amount of the porogen material is dissolved and rinsing the at least polycaprolactone structure flushes away porogen material and organic solvent. Advantageously, this step can be easily performed in the laboratory.

In another embodiment, the method of manufacturing a porous bioabsorbable composite scaffold further comprises the following steps after step (i):

(1) heating the at least polycaprolactone solution, and (2) stirring the at least polycaprolactone solution to ensure an even consistency.

Advantageously, ensuring that the at least polycaprolactone solution has an even consistency will improve the quality, reliability and consistency of the end product, as the density of polycaprolactone will be more constant throughout the scaffold.

In one embodiment, step (ii) includes immersing the porogen construct in the at least polycaprolactone solution for a period of at least 5 or 10 minutes.

In another embodiment, the porogen construct is immersed in the at least polycaprolactone solution for a period of at least 1, 6, 12 or 24 hours.

Advantageously, immersing the porogen construct for an extended period of time allows the at least polycaprolactone solution to completely infiltrate the interstices of the porogen construct, thereby allowing the formation of a more structurally regular scaffold. Immersing the porogen construct in the at least polycaprolactone solution for an extended period of time also results in the formation of a scaffold having smaller struts.

In one embodiment, step (ii) includes heating, microwaving, centrifuging and/or agitating the at least polycaprolactone solution and the immersed porogen construct.

Advantageously, heating, microwaving, centrifuging and/or agitating the at least polycaprolactone solution and the immersed porogen construct better facilitates the infiltration of the at least polycaprolactone solution into the interstices of the porogen construct.

In another embodiment, the method of manufacturing a porous bioabsorbable composite scaffold further comprises the following steps after step (v):

(1) (xvi) coating the at least polycaprolactone structure with bioactive glass powder.

Advantageously, introducing bioactive glass into the scaffold will stimulate both soft and hard tissue bonding to the scaffold when implanted. The bioactive glass will also help buffer the acidic environment caused by polycaprolactone degradation products. Varying the relative amounts of polycaprolactone and bioactive glass allows the degradation rate of the scaffold to be customised.

Coating bioactive glass powder to the scaffold is a simple and effective method of introducing bioactive glass into the scaffold, and furthermore, has the advantage of locating the bioactive substance at the tissue/cell interface.

In one embodiment, step (vi) includes placing the at least polycaprolactone structure in a container with an excess amount of bioactive glass powder and agitating the container in a Spe.>I.ID or ball mill.

Advantageously, agitating the container in a Spe.>I.ID or ball mill will ensure an even and thorough coating of bioactiveglass on the at least polycaprolactone structure.

In another embodiment, step (vi) includes dusting or blowing the at least polycaprolactone structure with heated bioactive glass powder.

Advantageously, as the heated bioactive glass powder contacts the surface of the at least polycaprolactone structure, it softens the at least polycaprolactone and firmly adheres to the surface. The at least polycaprolactone structure can be kept at room temperature or chilled before treatment.

In another embodiment, step (vi) includes liberally covering the at least polycaprolactone structure with bioactive glass powder and shaking off excess bioactive glass powder.

Advantageously, liberally covering the at least polycaprolactone structure with bioactive glass powder ensures a thorough coating of bioactive glass on the at least polycaprolactone structure.

In one embodiment, the method of manufacturing a porous bioabsorbable composite scaffold further comprises the following step after step (vi):

(1) (xvii) heating the at least polycaprolactone structure to between 40 and 80° C. for between 5 and 15 minutes.

In another embodiment, the at least polycaprolactone structure is heated to about 58° C. for about 10 minutes.

Advantageously, heating the at least polycaprolactone structure softens the at least polycaprolactone and allows the bioactive glass to firmly adhere to the surface.

In another embodiment, the method of manufacturing a porous bioabsorbable composite scaffold further comprises the following steps after step (v):

(1) (vi) coating the at least polycaprolactone structure with a slurry comprised of an organic solvent, a polymer and bioactive glass particles; and (2) (vii) allowing the slurry-coated at least polycaprolactone structure slurry to dry.

Advantageously, coating the slurry onto the surface of the scaffold is another method of coating the scaffold with bioactive glass. Slurry coating also provides a relatively even and thorough coating of bioactive glass. The small amount of organic solvent softens the surface of the at least polycaprolactone structure and allow the bioactive glass particles to firmly adhere to the surface. The addition of a polymer assists the binding and dispersion of the glass coating. Furthermore, the slurry will partially infiltrate into the pores of the scaffold and deposit some bioactive glass within the scaffold.

In one embodiment, the organic solvent comprises at least water, acetone or ethanol.

Advantageously, acetone is found naturally in the body as a product of the metabolism of fats and is therefore not toxic to the body in trace amounts, unlike many organic solvents.

Moreover, acetone is available at a relatively low cost compared to many other organic solvents. Ethanol has little or no harmful impact on the at least polycaprolactone structure. The type or types of solvent used in the formulation of the slurry also depends on the type of polymer used in the slurry.

In one embodiment the polymer comprises at least one polycaprolactone, polyvinyl alcohol or polyvinyl butyral.

Advantageously, the polymers listed above are biocompatible. Polycaprolactone is soluble in acetone and polyvinyl alcohol is weakly soluble in ethanol and polyvinyl butyral is soluble in ethanol. The addition of a polymer allows the glass to adhere more readily to the surface of the at least polycaprolactone structure.

In another embodiment, the method of manufacturing a porous bioabsorbable composite scaffold further comprises the following step after step (i):

(1) removing any undissolved solids from the at least polycaprolactone solution.

Advantageously, this step improves the accuracy in calculating the amount of polycaprolactone within each scaffold. Weighing the undissolved solids and comparing the result with the weight of the original amount of polycaprolactone added to the at least polycaprolactone solution enables the homogenous concentration of dissolved polycaprolactone to be calculated.

In another embodiment, the method of manufacturing a porous bioabsorbable composite scaffold further comprises the following steps prior to step (ii):

(1) adding bioactive glass powder into the at least polycaprolactone solution, and (2) mixing the at least polycaprolactone solution to form a substantially evenly (3) mixed suspension of bioactive glass powder within the at least polycaprolactone solution.

Advantageously, this allows bioactive glass powder to be incorporated into the main structure of the scaffold, rather than coated on the surface of the scaffold, allowing the degradation rate and mechanical properties to be more easily controlled. Furthermore, degradation will be more stable and consistent.

According to another embodiment of the present invention, a method of increasing the density of a porous bioabsorbable composite scaffold is provided, comprising the following steps:

(1) providing a porous bioabsorbable composite scaffold;

(2) compressing the scaffold; and (3) heating the scaffold for at least one second while compressed.

Advantageously, compressing the scaffold is a simple and effective method of increasing the density of the scaffold. Furthermore, this is a useful industrial processing method as compression is a process that can be reliably and consistently performed. Provided that the scaffolds provided are of consistent known density, this process allows scaffolds in a range of different densities to be obtained from the same original scaffold manufacturing process.

According to another embodiment of the present invention, a method of joining two porous bioabsorbable composite scaffolds is provided, comprising the following steps:

(1) providing two porous bioabsorbable composite scaffolds;

(2) applying warm saline to a side of each of the scaffolds;

(3) placing the moistened sides in contact with each other to form a join; and (4) fixing the join with light contact pressure.

Advantageously, the application of warm saline having a temperature close to or at the melting temperature of polycaprolactone softens the surface of the polycaprolactone and facilitates bonding and joining. Furthermore, this procedure is relatively simple and can be performed as required just prior to implantation or in the laboratory as desired. For example, a scaffold structure larger than the size of a unit piece may be required to cover a large wound. In another example, an irregularly shaped scaffold may be created by joining several scaffolds together to cover irregularly shaped wounds.

According to another embodiment of the present invention, a method of manufacturing a porous bioabsorbable composite scaffold having graded porosity is provided, comprising the following steps:

providing two or more porous bioabsorbable composite scaffolds, each of the scaffolds having a different density; and joining the two or more scaffolds together.

Advantageously, this is a simple and effective method of forming a scaffold of graded porosity. Furthermore, providing the gradient in discrete layers allows the steepness of the gradient to be easily controlled as desired.

According to another embodiment of the present invention, a method of manufacturing a porous bioabsorbable composite scaffold having graded porosity comprising the following steps:

providing three or more porous bioabsorbable composite scaffolds, each of the scaffolds having a different density; and joining the three or more scaffolds together in order of increasing density.

Advantageously, this is a simple and effective method of forming a scaffold of graded porosity. Furthermore, providing the gradient in discrete layers allows the steepness of the gradient to be easily controlled as desired.

According to another embodiment of the present invention, a method of manufacturing a tissue repair system is provided, comprising the following steps:

applying warm saline to a first side of the first membrane layer and to a first side of the intermediate layer, placing the first side of the first membrane layer in contact with the first side of the intermediate layer to form a first join, fixing the first join with light contact pressure, applying warm saline to a first side of the second membrane layer and to a second side of the intermediate layer, placing the first side of the second membrane layer in contact with the second side of the intermediate layer to form a second join, and fixing the second join with light contact pressure.

Advantageously, the application of warm saline having a temperature close to or at the melting temperature of polycaprolactone softens the surface of the polycaprolactone and facilitates bonding and joining. Furthermore, this procedure is relatively simple and can be performed as required just prior to implantation or in the laboratory as desired.

Figure 2:
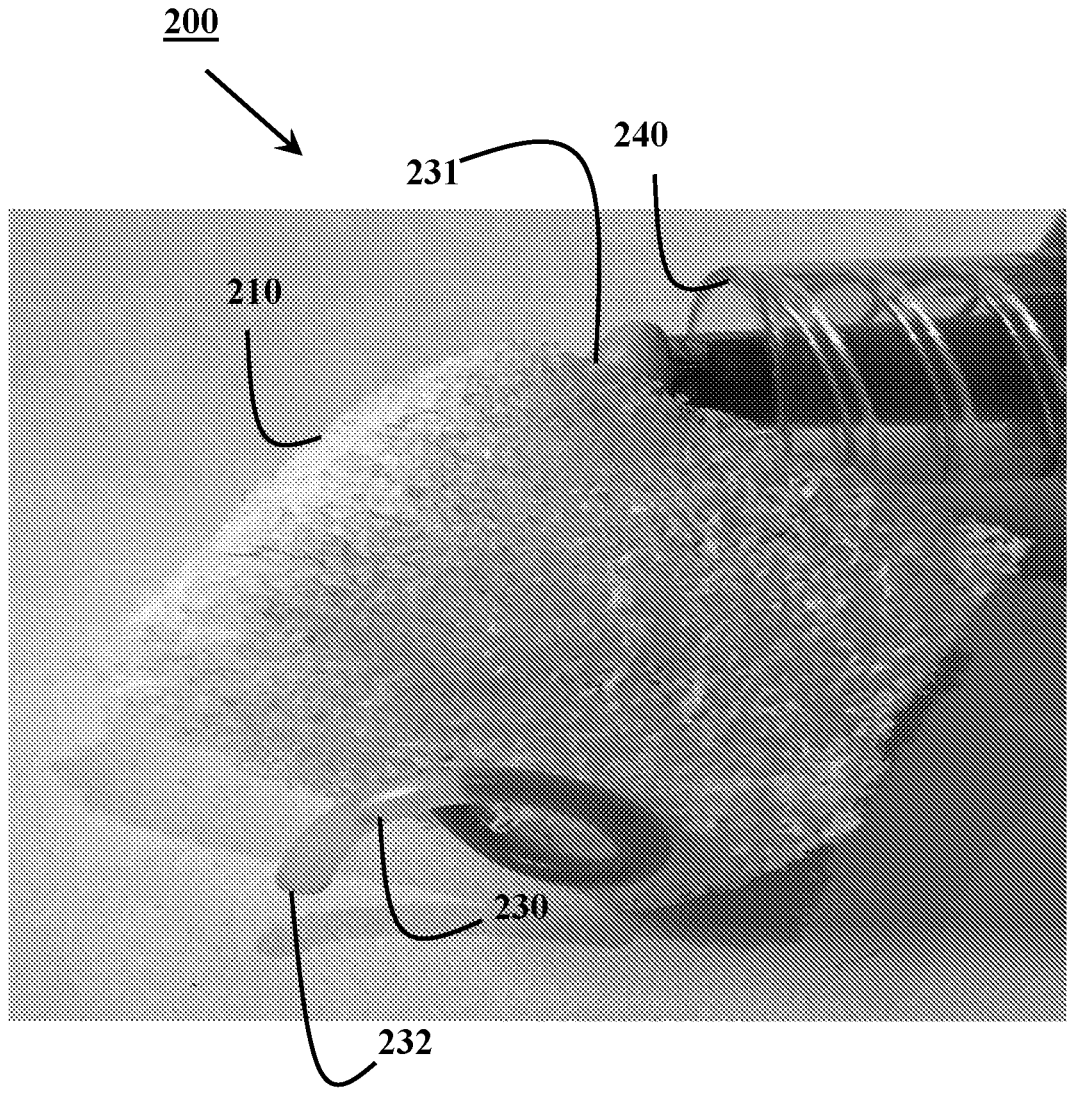
FIG. 2 is an image of a biocompatible scaffold including a biocompatible conduit filled with a therapeutic substance using a syringe.

FIGS. 1 to 3 depict embodiments of a reinforced biocompatible scaffold for facilitating integration of biological tissue. FIG. 1 depicts a schematic of an embodiment of the reinforced biocompatible scaffold. A 4×4 matrix array of filaments are embedded within a porous biocompatible scaffold. The 4×4 matrix array of filaments are also fixed to the biocompatible scaffold.

In this embodiment, the scaffold has 95 vol % of interconnected porosity space. In other embodiments, the scaffold may have within a range of 30-95% interconnected porosity space. The scaffold also includes 20 wt % of bioactive glass. In other embodiments, the scaffold may have between 0.1 to 35 wt % of bioactive glass. In other embodiments, the reinforced scaffold may comprise filaments and/or conduits with the range 0.01-50 vol % of the reinforced scaffold.

Rapid blood ingress into the high interconnected porosity bioacompatible scaffold facilies immediate fibrin matrix formation and subsequent healthy granulation tissue formation. This precursor tissue is able to differentiate based on microenvironment and scaffold mediated cues into the target tissue.

In a preferred embodiment the scaffold has 20 wt % bioactive glass with a trace amount of carbohydrate (>1%, containing sucrose, glucose, fructose). In the preferred embodiment, the polycaprolactone (linear aliphatic polyester), has a molecular weight of 80,000 GPC.

In one embodiment, the biocompatible scaffold can be made using the following process.

Fifty grams of PCL beads are heated in a microwave having a power output of 1200 Watts for 30 seconds (or until the opaque PCL beads turn substantially transparent, or translucent). The PCL has a molecular weight of 80,000 and a density of 1.15 g/cm3.

Acetone solution is then added to the clear beads to create a mixture with a ratio of 1:6 pcl-acetone solution by volume. In other embodiments, the pcl-acetone solution mixture ratio is or in the range of 1:4-1:10 by volume.

The pcl-acetone mixture is placed in a bag made of low-density polyethylene and then the bag is sealed. The pcl-acetone solution mixture is then masticated while in the LDPE sealed bag using a rolling press at approximately 20 revolutions per minute or by hand until the mixture is even. In this way, no bacteria or other undesirable foreign material will not be introduced into the polycaprolactone-acetone solution mixture as the rolling press or hand will not directly contact the mixture. This process takes approximately 3 to 10 mins for 50 g of PCL.

The pcl-acetone mixture can be microwaved for 5 seconds if the pcl-acetone solution mixture begins to cool and turn opaque. The solution is then diluted with acetone to a desired concentration. In this embodiment, the desired solution is 17.7 vol % pcl in the pcl-acetone solution. In other embodiments, the solution may be in the range of 10 to 50 vol % of pcl in the pcl-acetone solution.

Microwaving the pcl-acetone mixture is advantageous over heating the mixture in an oven as not only is the mixture evenly heated in a microwave it takes less time and the mixture dehydrates less in an oven.

Furthermore, when PCL is microwaved, energy is more focused on the polymer chains present in the mixture and the microwaving process efficiently (i.e. in relatively short time) and evenly mobilizes the polymer chains than when heating the mixture in an oven. Hence, the inherent molecular makeup of PCL is suited to heating using a microwave.

Also, when an oven is used to heat PCL, the outside of the polymer tends to oxidise which tends to stiffen part of the mixture As oxidizing changes the mechanical properties of the mixture, it is difficult to masticate into an evenly formed mixture and therefore, scaffold have uniform mechanical properties even when heat is applied in a later step. Oxidising tends to cause part of the mixture to behave as a thermosetting polymer while microwaving for prescribed periods of time results in the pcl remaining thermoplastic. Also, acetone or other organic solvent is used to mobilise the polymer chains of the PCL within a solution and requires mixing. With microwaving, less acetone is required to sufficiently mobilize the polymer chains for forming (for example, into a rod or to infuse bioactive glass.

At this stage, the solution can be stirred using a magnetic stirrer. This step introduces fluid-shear leading to polymer chain scission prior to forming the scaffold structure. Stirring reduces the effective polymer molecular weight. The bioresorbability rate can be increased by increasing the time for which the solution is continuously stirred at or above 60 degrees Celsius. Hence, this method allows for better control of the rate of bioresorbability.

If a lesser rate of bioresorbability is required, the solution can be stirred continuously for less than a day or for a day for example. This leads to a relatively tougher scaffold being formed than if the solution is stirred for a longer period of time.

If a faster-degrading scaffold is required, then at this point the solution can be magnetically stirred (at approximately 100 rpm) for up to 5 days.

As described above, to create the porous structure a sucrose porogen construct produced by laser sintering, for example, can be immersed into the solution. As mentioned above, dissolving at least polycaprolactone (PCL) in an organic solvent to form an at least polycaprolactone solution and immersing the porogen construct in the at least polycaprolactone solution facilitates the infiltration of polycaprolactone into the interstices of the porogen construct. The porogen construct provides a template or a negative mold for the scaffold.

To speed this process, the porogens with PCL solution can be microwaved for 5 to 10 seconds to reduce the viscosity of the solution, drive out entrapped air and heat the sucrose porogen to increase surface energy for rapid and more complete infusion/infiltration of the solution within the porogen.

The scaffold can then be batch coagulated by immersing the porogens in cold water, allowing skins to be formed. The skins are then peeled of the scaffold to remove barriers to cross-diffusion of acetone, water and sucrose within the solution while the PCL is coagulated into a hierarchical scaffold. The scaffold has a porosity of 95% by volume and includes with large pores (sized at approximately 500 microns) and struts.

As mentioned above, the scaffold may then be coated by thermally bonding (at 60 degrees Celsius) bioactive glass powder (or fibre or spheres, and other additives) to the scaffold to create an evenly dispersed bioactive glass coating. The scaffold can be heated in the microwave until outer surfaces of the scaffold are softened or "sticky" i.e. will tend to adhere to bioactive glass or PCL or other polymer, for example. This can be at a temperature just under the melting temperature of PCL. The outer surfaces of the scaffold tend to melt earlier than the inner parts as they have less bonds other parts of the scaffold. The scaffold can then be evenly coated with bioactive glass powder by for example, rolling the "sticky" scaffold in bioactive glass powder. An advantage of this is that as the bioactive glass is not mixed into the mixture when it is in solution form, therefore, the user does not need to mix the mixture extensively and monitor the mixture continuously to ensure that the bioactive glass is evenly dispersed throughout the entire mixture.

Advantageously, less energy needs to be put into the process to form the biocompatible scaffold. The above method is also suitable for small batch synthesis of biocompatible scaffolds. Less raw material e.g. PCL, solvent, bioactive glass is required.

Conventionally, batching processes to create scaffolds are configured to produce scaffolds at industrial scale. Such processes typically require large amounts of raw material e.g. 20 kg of PCL pellets, larger volumes of solvent are required and the PCL typically undergoes more fluid shear which results in chain scission and reduction in PCL molecular weight, eventually resulting in a less robust scaffold and less control of bioresorbability.

Also, as smaller scaffolds can be rapidly formed using this process, the above method is suitable for creating patient-specific implants in a short period of time. The implants can be prepared during surgery or just before surgery. Thus, the surgeon is not limited to selecting from off the shelf products which may be inferior for the particular purpose.

In another embodiment, the scaffold may then be used as a generic shaped scaffold, or packaged then transformed while in packaging into to a desired size, shape, density, mechanical property. The shape may formed using thermoplastic methods but through a pliable thermally stable packaging, while using an external shaping tool (also thermally stable). This can be inverse-anatomically-shaped to form an anatomic scaffold.

The scaffold resulting from this process can also be formed into a precursor material for another forming process for example, by heating the scaffold using a microwave (for 10 seconds) (or until the solution is clear or glistening). This heated mixture can then be masticated by a rolling press or manually to form a precursor material for drawing, extruding, pultruding or molding one or more of filaments, conduits, fibre-tow, non-woven sheet or fabric or a 3D non-woven scaffold.

For example, to produce a 3D non-woven scaffold for a 3D ear the precursor material is combined with sucrose particles of 200-300 µm diameter and larger size having 500 µm diameter). In a preferred embodiment, 20 vol % scaffold precursor is combined with 78 vol % sucrose particles and 2 vol % distilled water.

In the preferred embodiment for the type of crystalline sucrose added, the ratio of fine to coarse sucrose particles is 1:1. In other embodiments, it may also be in the range of 3:1-1:10. In another embodiment the sucrose may be substituted with amorphous carbohydrate (containing a mix of sucrose, fructose, glucose, flavanoids) of similar size specification.

Extra bioactive glass powder (up to 20 wt %) or other additives may also be added at this step so as to preserve the ratio of precursor material to sucrose and water.

The resultant mixture is briefly agitated or vibro-mixed for 5-10 seconds to ensure uniform distribution of constituents of the mixture.

The mixture is then microwaved (at 1200 Watt) for 9-10 seconds for a 25 gram mixture and for longer (up to 1 min) if the mixture is larger e.g. 500 g. Then the mixture is immediately masticated (at 30 rpm) for 20-30 seconds using a rolling press or manually for smaller mixtures.

This mixture is then placed or injected into a mold and immediately submerged in cool water to allow the water in and the sucrose to dissolve out leaving behind the desired scaffold.

The porous biocompatible scaffold made using a variation of the above method can be configured to have a tensile strength (MPa) between 1.5 to 200 MPa.

The porous biocompatible scaffold made using a variation of the above method can be configured to have a compressive strength (MPa) between 0.5 to 1000 MPa.

The porous biocompatible scaffold made using a variation of the above method can be configured to have an interconnected porosity within the range of 10 to 98%.

The porous biocompatible scaffold can be configured to be suitable for soft tissue integration or hard tissue integration.

In an embodiment, biocompatible filaments can be drawn from heated precursor material as described above at a temperature of 80 degrees Celsius at a rate of 10 mm/s. In another embodiments, the filaments can be drawn at a temperature in the range of 60-95 degrees Celsius at a rate within the range of 1-15 mm per second.

The filaments can be strain crystallised to have a higher percentage of crystallinity. The strain-crystallized filaments are clear or translucent. To achieve a strain crystallised filament, the filament can be drawn at 20 degrees Celsius at a rate of 20 mm/s. In other embodiments, the filaments can be drawn at a temperature within the range of 0-58 degrees Celsius and at rate of within the range of 15-500 mm/sec to achieve a strain crystallised filament.

In another embodiment, the filaments can be produced by an electrospinning process using electrospinning apparatus (not shown). The rate of drawing can be in the range of 15-500 mm. A spool and a plate behind the spool is earthed while the rest of the spinning chamber is electrically insulated using a dry acrylic box to allow for efficient movement of the fibres to the spool for collection.

The at least one biocompatible filament and/or conduit is made of polycaprolactone. The polycaprolactone can have a molecular weight corresponding to 80,000 measured using gel permeation chromatography. The at least one biocompatible filament and/or conduit may include trace amounts of carbohydrate such as less than 1% of sucrose, glucose and fructose. The at least one biocompatible filament can include 20 wt % of bioactive glass. In other embodiments, the at least one biocompatible filament can include a proportion of bioactive glass within the range of 0 to 30 wt %.

The diameter of the at least one biocompatible filament may be 20 µm. In other embodiments, the diameter of the at least one biocompatible filament may be in the range of 1 to 50 µm. In other embodiments the diameter of the at least one biocompatible filament can be greater than 50 µm.

Filament and/or conduits may be drawn using a conventional drawing process suitable for drawing plastics into thread or filaments. Such methods typically involve securing one end of a precursor material in a particular shape such as a rod and pulling or drawing the plastic from an opposite end of the precursor material. Typically, the opposite end is connected to a rotating spool which simultaneously draws and collects the drawn filament. Typically, the higher the rate of revolution of the spool, the thinner the diameter of the drawn filament.

An embodiment of a method of making a biocompatible filament or conduit is now described.

Precursor material is formed from the base scaffold as mentioned above, the base scaffold in this embodiment includes polycaprolactone (linear aliphatic polyester) with a molecular weight of 84,000 g/mol and a density of 1.15 g/cm3.

Precursor material is then formed using the following method:

The scaffold formed as described above, from 50 grams of PCL, is heated.

The scaffold-powder mixture is heated (in a microwave having a power output of 1200 W) for 50 seconds of exposure to form a molten mixture.

The molten mixture is masticated for approximately 20 seconds using a roller system to eliminate any agglomerates and ensure distribution of powder in the mixture.

Alternatively, if the proportion of bioactive glass in each filament is to be increased or if the scaffold does not include any bioactive glass, then bioactive glass powder (such as 45S5 bioactive glass) is added to the molten mixture. The powder can have a diameter within the range of 10-15 microns or µm.

The mixture is plastically formed or extruded while molten, into a rod, preferably with aspect ratio 4:1 (or in the range of 3:1 to 10:1) then allowed to cool to standard lab conditions (22 degrees Celsius).

The above process can be modified to draw biocompatible conduits having internal channels. In this embodiment, instead of forming the mixture into a rod, the mixture can be formed into a cylinder having an internal channel.

Filaments and/or conduits may be drawn using a conventional drawing process suitable for drawing plastics into thread or filaments.

To form filaments using a conventional drawing process, the rod including precursor material is creased or gently crimped in the centre of the rod using a fastening clamp to support the precursor rod during the drawing process.

The rod has a first end and a second end. A first end of the rod is then clamped in a holder and the other end is fastened to a rotating spool.

The spool is rotated so that filaments are drawn from the rod at a rate of 20 mm/s. In other embodiments, the filaments can be drawn at a rate within the range of 10-500 mm/s.

In other embodiments, to draw a predominantly amorphous filament or conduit, the drawing rate can be within the range 1 to 15 mm per second and at a temperature within the range of 60 to 95 degrees Celsius. In a preferred embodiment, the filament or conduit can be drawn at a rate of 10 mm/second at a temperature at approximately 80 degrees Celsius.

In yet other embodiments, to draw a predominantly strain crystallised filament or conduit, the drawing rate is within the range 15 to 500 mm/second and at a temperature within the range of 0 to 58 degrees. In a preferred embodiment, the filament or conduit can be drawn at a rate of 20 mm/second at a temperature at approximately 20 degrees Celsius.

The drawn filament or conduit is collected onto the spool and removed from the clamp. Individual filaments or conduits having a desired length can be cut from the drawn filament using for example, scissors.

If a non-strain crystallized filament is desired, the rod can first be warmed at the crimped zone to allow molten polymer composite to be drawn.

Alternatively, the strain-crystallized filament can be clamped and held with gentle tension, then heat treated at 58-60 deg C. for 5 seconds, or until relaxation of the filament is observed.

If the strained-crystallized filament is returned into the relaxed (more amorphous) form, then a finer diameter strain-crystallized filament can be formed by drawing a thinner filament from the initially strain-crystallized filament.

Helical filaments can be formed by winding a drawn filament around a core that is non-adhesive to the filament, such as an elongate metal cylinder and immersing the filament and core in heated water at 58 degrees Celsius for approximately 5 seconds. Advantageously, helical filaments, due to their flexibility can provide a reinforced scaffold with a relatively lower directional stiffness than straight filaments. Advantageously, helical filaments can result in a reinforced scaffold close to that of soft tissue.

Thus, a biocompatible scaffold including an array of helical filaments can be used for soft tissue integration.

By contrast embedding a plurality of straight filaments within the scaffold can result in a scaffold of high stiffness in the axial direction of the filament. The stiffness of the reinforced scaffold can therefore, be configured or tuned to that of bone for bony integration. The stiffness of the reinforced scaffold can also be configured or tuned to be less than the average stiffness of bone.

An advantage of using strain crystallised fibre elements are that they can be used to selectively shrink or actuate the scaffold directionally when heated to approximately 57 to 60 degrees Celsius. When the filaments are strained to an extent near natural biomechanical strain, piezo electricity is generated with potential to enhance and guide tissue regenerative events. Advantageously, bone formation known to be accelerated with piezo-electric stimulus. Therefore, the reinforced scaffold can be tuned to provide an environment conducive to cell development of a specific type of cell as well as an environment conducive to biological tissue integration within the scaffold.

One or more biocompatible conduits can be embedded within the scaffold as shown in figure x. In this embodiment, the at least one conduit has an outer diameter of 1.2 mm and an inner diameter of 0.6 mm. In other embodiments the at least one conduit can have an outer diameter within the range of 0.5 mm to 1.7 mm.

In other embodiments the at least one conduit can have an inner diameter within the range of 0.1 mm to 1.2 mm. In other embodiments the at least one conduit can have an inner diameter less than 0.1 mm or greater than 1.2 mm.

The at least one biocompatible conduit has a first open end extending to a second, sealed end. The second end of the conduit can be sealed by heating the end and crimping the end using a crimping tool. have a sealed end to retain a substance within the conduit. The substance can be a therapeutic substance such as a medicine. The at least one biocompatible conduit can be configured to be semi-permeable to allow movement of cells, factors, bodily fluids, gases and other biological material through the conduit. For example, the at least one biocompatible conduit can be made of semi-permeable material. This will allow medicine to slowly leach out of the semi-permeable material after a therapeutic medicine is sealed within the conduit. Therefore, the conduit can be configured to be drug eluting.

For example, a reinforced scaffold 200 including at least one biocompatible conduit 230 with a sealed end 232 can be provided to a user such as a nurse or a surgeon. The first end of the conduit 231 is located near a surface of the scaffold as shown in FIG. 2. The user can then inject a desired medicine into a first, open end 231 of the conduit 230 to fill the conduit 230 with medicine using a syringe 240. After the medicine has been inserted, the first, open end 231 of the conduit 230 can be sealed. The reinforced scaffold 200 can then be implanted into a subject such as a patient. Being able to fill and seal the capillary at the time of implantation can help avoid regulatory challenges associated with devices including therapeutic substances available off the shelf, the poor shelf life of certain therapeutic substances and therefore, limited treatment options.

In another embodiment, the biocompatible conduit could be loaded with other regenerative step cells from blood or fat for enhanced expression of desired proteins such as Brain-derived neurotrophic factor (BDNF), for example. The biocompatible conduit could be loaded with other therapeutic materials in other embodiments such as stem cells. The biocompatible conduit can be provided in a helical shape.

After filaments and/or conduits are embedded within the scaffold, they can be attached or fused to scaffold by solvent welding using an acetone solution. In an example, the filaments can be fused to the scaffold by solvent welding i.e. applying a solution comprising acetone and 10 wt % poly-caprolactone to the scaffold after the filaments and/or conduits have been embedded within the scaffold. In another example, fusing each filament to the scaffold to fix each filament within the scaffold may include gently spot welding each filament to the scaffold using water selectively applied at a temperature within the range of 58 degrees Celsius to 70 degrees Celsius. This is useful for filaments which are not strain-crystallised.

In other embodiments, the filaments and/or conduits can be fused to the scaffold by selectively spot welding using heated saline at or just under the melting temperature of the scaffold i.e. approximately 58 degrees Celsius or immersing the scaffold with embedded filaments in saline heated at approximately that temperature. In other examples, the filaments and/or conduits can be fused to the scaffold using ultrasound and/or focussed light or laser at discrete points of each filament such as at the ends of each filament.

In another embodiment (not shown) the filament can be formed from pure polycaprolactone in the core and coated with bioactive glass fibre to form a macro-composite. This can be carried out by dipping the fibre for 5-10 seconds in an acetone-bioactive glass suspension (10 vol %), or in a PCL-acetone-bioactive glass suspension containing 10 wt % PCL (in the range of 1-20 wt % PCL) and 10 wt % bioactive glass (or in the range of (0-20 wt % bioactive glass).

FIG. 1 illustrates an embodiment where a 2×2 matrix array of filaments 120 have been embedded into a scaffold 110. The filaments 120 are equally spaced from each other and extend parallel to each other through the entire thickness of the scaffold 110. Advantageously, the filaments 120 impart an increase in strength in the longitudinal or axial direction of each filament. The average longitudinal direction of the filaments is indicated by the Y-axis in FIG. 1. No significant change is made to the strength of the scaffold in the X direction as a result of adding these filaments. Hence, the filament can introduce directional mechanical properties within the scaffold 110 and mechanically reinforce the scaffold.

The scaffold has a porosity of 95%. Advantageously, the reinforced scaffold had a 9 fold increase in stiffness compared to the scaffold without the embedded filaments in the axial direction of the filaments. The filament reinforced scaffold has a small reduction of less than 1.5% reduction in porosity due to the presence of the filament. There is a negligible change in the strength in other directions aside from the axial direction of the filaments.

To embed the filaments into the scaffold, several methods can be used. In one example, the filament can then be threaded into the scaffold as a tow using a needle-array jig or a jig configured to insert helical filaments into the scaffold.

In an embodiment, the number of filaments in the tow is 20 (in another embodiment, the number of filaments in a tow can be within the range 10-50). In this embodiment, the diameter of the filament is 20 microns. In other embodiments the diameter of the filament can be in the range of 1-50 micron. The fibres can be straight (or 2D crimped or possess a helical wind.

In another embodiment, embedding the at least one biocompatible filament includes threading one or more of the at least one biocompatible filament through the eye of a sewing needle, inserting the needle into the scaffold and moving the needle through the scaffold and then, removing the needle while leaving the filament remaining in the scaffold.

In another embodiment, embedding a helical biocompatible filament and/or conduit into the scaffold includes:

Providing a helical wire substantially identical in shape and size to a filament of the at least one biocompatible filament, the helical wire having a first end and a second end.

Attaching one end of a helical biocompatible filament to the second end of the helical wire.

Rotatably inserting the helical wire into one surface of the scaffold to create a helical channel to house the biocompatible filament within the scaffold.

Removing the helical wire from the scaffold by continuing to rotate the helical wire through the scaffold until the helical channel is filled with the biocompatible filament and the helical wire exits one surface of the scaffold and is completely out of the scaffold.

Detaching the helical wire from the biocompatible filament.

FIGS. 3A to 3D illustrate a method of embedding and fixing biocompatible filaments into a biocompatible scaffold using a jig or apparatus 1000.

Figures 3A, 3B, 3C:
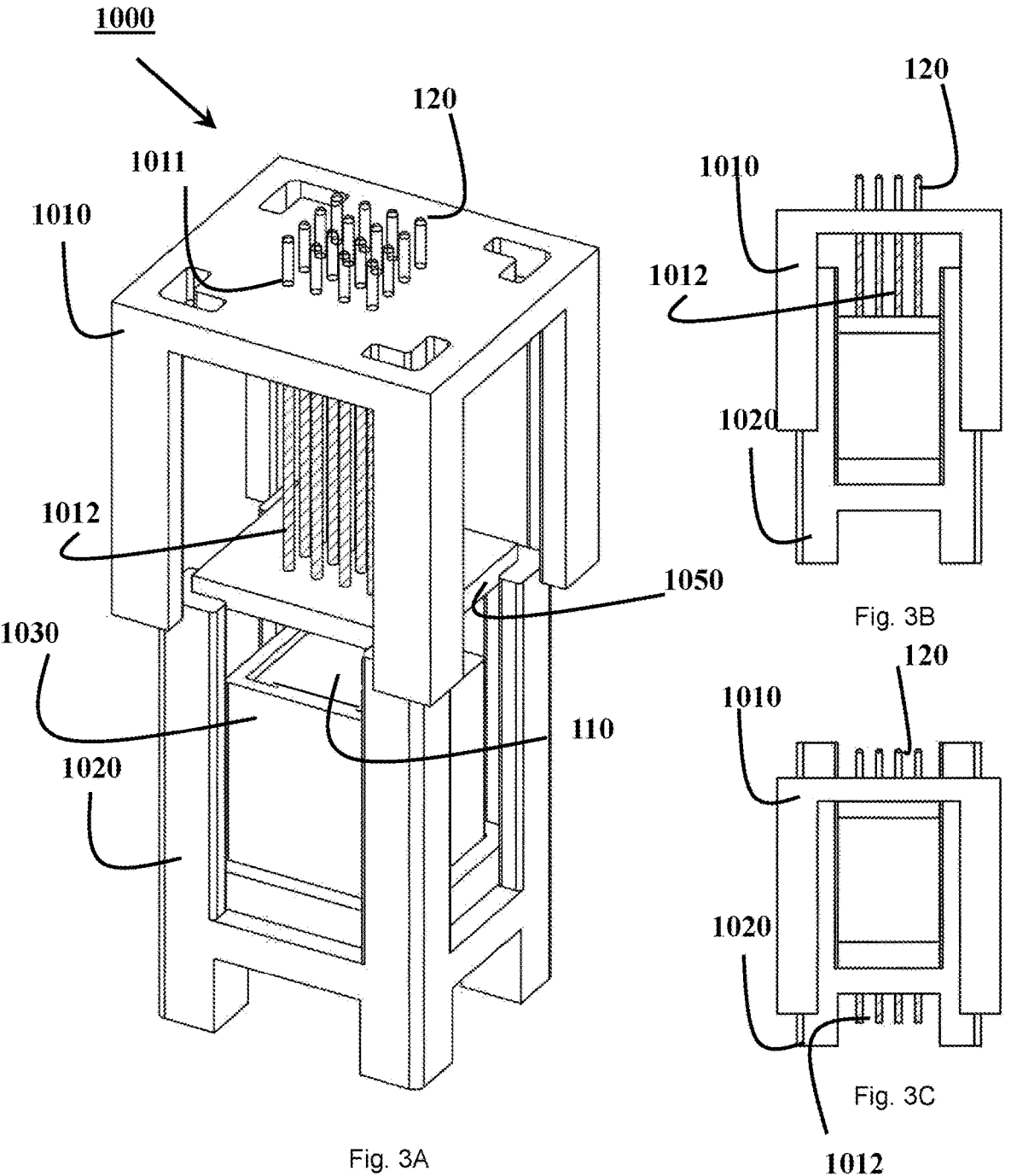
FIG. 3 is an image of a reinforced scaffold taking using a scanning electron microscope showing a strut within the scaffold

FIG. 3A shows an exploded view of an apparatus 1000 for embedding the arrangement of bioglass filaments into the scaffold. A first part 1010 of the apparatus has a rectangular top plate 1015 including an arrangement of apertures 1011 extending through the entire thickness of the top plate, the arrangement of apertures 1011 corresponding to the desired arrangement of filaments 120 to be inserted into the scaffold 110. A cannulated needle 1012 is fixed inside each aperture such that a filament 120 can be inserted into channel of each cannulated needle 1012 from above the first part 1010. As the filaments 120 have diameters much smaller than the diameter of the channel within each needle, a support 1050 is positioned and held under the layer of needles 1012 to prevent the filaments 120 falling out of the needles.

The first part 1010 of the apparatus 1000 has four legs extending downwardly from each corner of the top plate 10105. The second part 1020 of the apparatus 1000 has a rectangular base plate and four columns extending upwardly from each corner of the base plate. Each column also extends into a leg extending below the base plate. The second part 1020 also includes a removable holder 1030 having a cavity for housing and supporting the scaffold 110 while the cannulated needles 1012 pierce the scaffold 110. In other embodiments, the holder 1030 can be of adjustable size. The base plate has a hole located approximately in the centre of the base plate that is configured to allow needles 1012 and filaments 120 to extend through the base plate yet retain the holder 1030 above the base plate.

The holder 1030 is configured to allow needles 1012 and the filaments 120 to pierce through the scaffold 110.

An inside surface of each leg of the first part 1010 has a female part configured to mate with a male part on the outside surface of a corresponding leg of the second part 1020 so as to correctly position the first part 1010 of the apparatus relative to the second part 1020 of the apparatus and so, guide movement of the legs of first part 1010 relative to and the second part 1020 when the top plate 1015 is brought close to the base plate. The top plate 1015 is larger than the bottom plate and has four leg holes extending through the thickness of each plate configured to allow the four legs of the second part to extend through each of the leg holes when the four legs of the second part 1020 are aligned with the four corresponding holes in the top plate. Each hole is located adjacent a corner of the top plate.

The scaffold 110 is placed within the cavity of the holder.

Each hole in the rectangular plate has a diameter that is the same size or slightly larger than a filament yet smaller than the outer diameter of each cannulated needle.

A filament is inserted into each of the holes in the top plate and into the channel of a cannulated needle located under the respective hole in the top plate. As shown each filament is longer than each cannulated needle.

The top part being correctly oriented in relation to the bottom part is then moved towards the base plate as shown in FIG. 3B and in FIG. 3C. Movement of the first part towards the bottom part forces the cannulated needles into the scaffold. The first part is moved until the needles 1012 have completely pierced the scaffold 110. In the illustrated embodiment, the arms of the second part extend through the respective holes in the top plate.

Figures 3D, 3E:
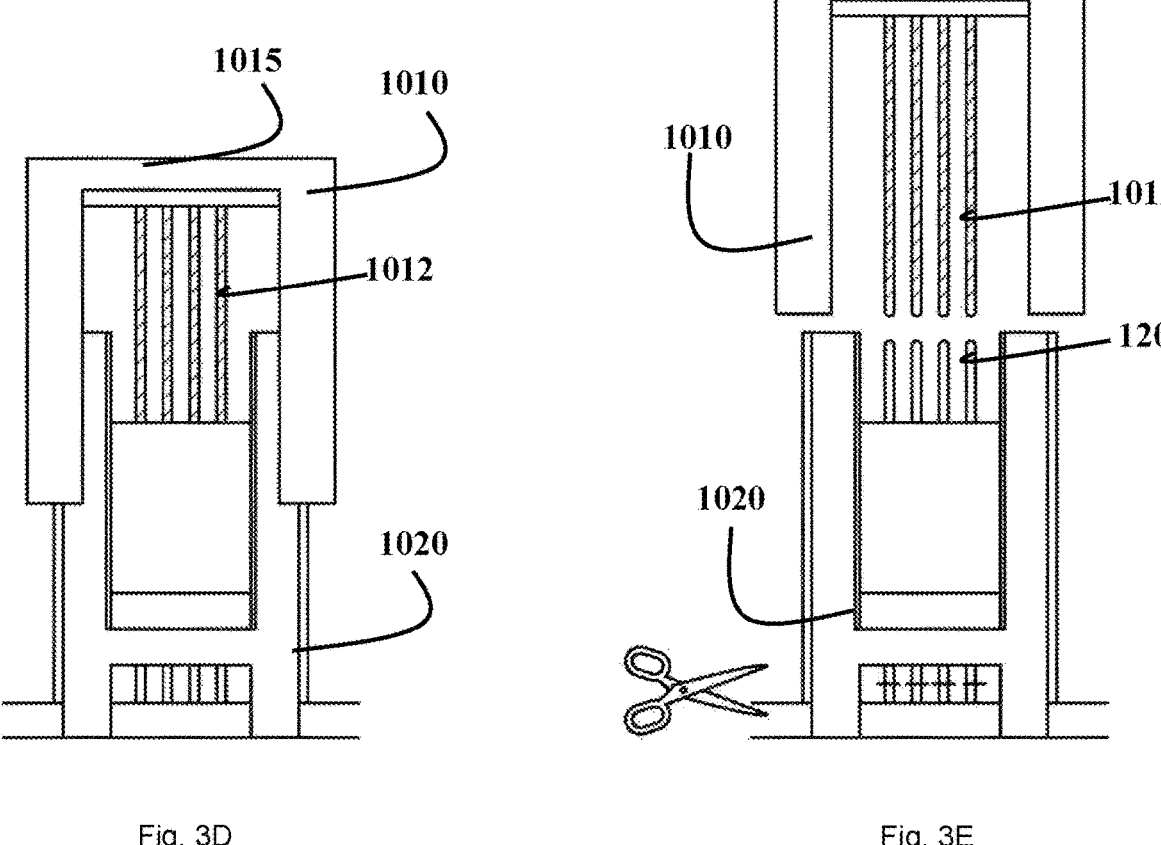

To remove the cannulated needles 1012, a user grips the top part of the apparatus and gently moves the top part upwardly and away from the bottom part as shown in FIG. 3D. The filaments which have a smaller diameter than the inner diameter of each cannulated needle remain within the scaffold as shown in FIG. 3E.

Using this apparatus 1000, in another embodiment multiple scaffolds 110 can be stacked within the holder 1030 and simultaneously embedded with an array of filaments 120.

The filaments 120 can then be fused or fixed to the scaffolds 110 using one of the methods discussed above, such as solvent welding.

After the needles are removed, the ends of the filaments protruding out of the scaffold can be trimmed as shown in FIG. 3E.

It is envisaged that the arrangement of filaments and/or conduits can include the number of filaments and/or conduits, spacing between adjacent filaments and/or conduits, types of filaments (e.g. amorphous, strain crystallised, linear, helical, straight) and distribution of these types of filaments within each biocompatible scaffold can be varied to achieve different mechanical properties of the reinforced scaffold.

The length, diameter and relative orientation of filaments within the biocompatible scaffold can be varied. The biocompatible materials used to make the filaments can also be varied.

In an embodiment, the arrangement of filaments and/or conduits can be configured such that the stiffness of the biocompatible composite scaffold is under that of an average stiffness of bone.

For example, the arrangement of filaments and/or conduits can be configured such that the stiffness of the biocompatible composite scaffold is under that of an average stiffness of cartilage.

For example, the arrangement of filaments and/or conduits can be configured can be configured such that the stiffness of the biocompatible composite scaffold is under that of an average stiffness of soft tissue.

For example, the arrangement can be configured such that the stiffness of the biocompatible composite scaffold is under that of an average stiffness of soft tissue.

While the invention has been described with reference to a number of preferred embodiments it should be appreciated that the invention can be embodied in many other forms.

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

The invention claimed is:

1. A method of making a porous biocompatible scaffold, comprising:
   providing a composition comprising one or more biocompatible polymer materials, wherein the one or more biocompatible polymer materials comprises solid polycaprolactone and wherein polycaprolactone is present within a range of 10 to 50% w/v;
   heating the composition comprising the one or more biocompatible polymer materials to provide a heated at least partially fluid composition comprising the one or more biocompatible polymer materials;
   mixing the at least partially fluid composition comprising the one or more biocompatible polymer materials and one or more organic solvents to provide a heated fluid composition;
   providing a porogen construct;
   combining the porogen construct and the heated fluid composition to form a temporary composite;
   immersing the temporary composite in water; and
   allowing a membrane to at least partially form on at least part of a surface of the temporary composite;
   removing the at least partially formed membrane from the at least part of the surface of the temporary composite;
   allowing ingress of water substantially throughout the temporary composite;
   allowing coagulation of the at least one or more biocompatible polymer materials within the porogen construct to form a coagulated scaffold;
   removing the water, porogen construct, and one or more solvents from the temporary composite to provide a scaffold having a hierarchical interconnected porosity, wherein the scaffold has a porosity within the range of 30 to 95% of the volume of the scaffold; and
   introducing an arrangement of one or more biocompatible filaments and/or at least one biocompatible conduit into the scaffold to reinforce the porous scaffold,
   wherein the at least one biocompatible conduit has a first open end and a second open end, the at least one biocompatible conduit is embedded such that the first open end is at a surface of the scaffold to enable filling of the conduit with a substance, and
   wherein the second open end is sealed during a surgery to enable drug elution.

2. The method of claim 1, wherein the organic solvent is acetone and mixing the heated polycaprolactone and organic solvent to provide a mixture having a proportion of approximately 17% w/w concentration of polycaprolactone.

3. The method of claim 1, further including:
   heating the coagulated scaffold at a temperature just under the melting temperature of the scaffold such that the outer surfaces of the scaffold are softened; and
   coating the coagulated scaffold with bioactive glass powder.

4. The method of claim 3, wherein the bioactive glass powder has a diameter within the range of 10 μm to 15 μm.

5. The method of claim 1, wherein the one or more filaments and/or the at least one biocompatible conduit is helical.

6. The method of claim 5, further including embedding the one or more biocompatible filaments and/or at least one biocompatible conduit within the biocompatible scaffold, and fusing the one or more biocompatible filaments and/or at least one biocompatible conduit within the scaffold.

7. The method of claim 6, wherein embedding the one or more biocompatible filament and/or the at least one biocompatible conduit comprises:

providing a helical wire substantially identical in shape and size to the at least one helical filament or conduit, the helical wire having a first end and a second end;

attaching one end of a helical biocompatible filament to the second end of the helical wire;

rotatably inserting the helical wire into the scaffold to create a helical channel to house the biocompatible filament within the scaffold;

removing the helical wire from the scaffold by continuing to rotate the helical wire through the scaffold until the path is filled with the biocompatible filament and the helical wire is out of the scaffold; and detaching the helical wire from the biocompatible filament.

8. The method of claim 6, wherein fusing the one or more biocompatible filaments to the scaffold to fix each filament within the scaffold includes solvent welding using a solution comprising acetone and polycaprolactone.

9. The method of claim 5, wherein fusing each filament or conduit to the scaffold to fix each filament or conduit within the scaffold includes spot welding the filament by applying water or saline at a temperature within the range of 60 degrees Celsius to 70 degrees Celsius to each filament or conduit.

10. The method of claim 1, wherein the porosity of the biocompatible scaffold comprises an interconnected porous structure comprising a distribution of macropores, mesopores and nanopores.

11. A method of making a porous biocompatible scaffold, comprising:

providing a composition comprising one or more biocompatible polymer materials, wherein the one or more biocompatible polymer materials comprises solid polycaprolactone and wherein polycaprolactone is present within a range of 10 to 50% w/v;

heating the composition comprising the one or more biocompatible polymer materials to provide a heated at least partially fluid composition comprising the one or more biocompatible polymer materials;

mixing the heated at least partially fluid composition comprising the one or more biocompatible polymer materials and one or more organic solvents to provide a heated fluid composition;

providing a porogen construct;

combining the porogen construct and the heated fluid composition to form a temporary composite;

immersing the temporary composite in water;

allowing a membrane to at least partially form on at least part of a surface of the temporary composite;

removing the at least partially formed membrane from the at least part of the surface of the temporary composite;

allowing ingress of water substantially throughout the temporary composite;

allowing coagulation of the at least one or more biocompatible polymer materials within the porogen construct;

removing the water, porogen construct, and one or more solvents from the temporary composite to provide a scaffold having a hierarchical interconnected porosity, wherein the scaffold has a porosity within the range of 30 to 95% of the volume of the scaffold;

introducing an arrangement of one or more biocompatible filaments and/or at least one biocompatible conduit into the scaffold to reinforce the porous scaffold, wherein the one or more filaments and/or the at least one biocompatible conduit is helical; and embedding the one or more biocompatible filaments and/or at least one biocompatible conduit within the biocompatible scaffold, and fusing the one or more biocompatible filaments and/or at least one biocompatible conduit within the scaffold, wherein embedding the one or more biocompatible filament and/or the at least one biocompatible conduit comprises:

providing a helical wire substantially identical in shape and size to the at least one helical filament or conduit, the helical wire having a first end and a second end;

attaching one end of a helical biocompatible filament to the second end of the helical wire;

rotatably inserting the helical wire into the scaffold to create a helical channel to house the biocompatible filament within the scaffold;

removing the helical wire from the scaffold by continuing to rotate the helical wire through the scaffold until the path is filled with the biocompatible filament and the helical wire is out of the scaffold; and detaching the helical wire from the biocompatible filament.

12. The method of claim 11, wherein the organic solvent is acetone and mixing the heated polycaprolactone and organic solvent to provide a mixture having a proportion of approximately 17% w/w concentration of polycaprolactone.

13. The method of claim 11, further including:

heating the coagulated scaffold at a temperature just under the melting temperature of the scaffold such that the outer surfaces of the scaffold are softened; and coating the coagulated scaffold with bioactive glass powder.

14. The method of claim 13, wherein the bioactive glass powder has a diameter within the range of 10 μm to 15 μm.

15. The method of claim 11, wherein the porosity of the biocompatible scaffold comprises an interconnected porous structure comprising a distribution of macropores, mesopores and nanopores.

* * * * *